(12) United States Patent
Choi et al.

(10) Patent No.: US 8,957,196 B2
(45) Date of Patent: Feb. 17, 2015

(54) VECTOR AND EXPRESSION CELL LINE FOR MASS PRODUCTION OF RECOMBINANT PROTEIN AND A PROCESS OF PRODUCING RECOMBINANT PROTEIN USING SAME

(75) Inventors: In Young Choi, Youngin-si (KR); Chang Hwan Kim, Gyeonggi-do (KR); Hyun Ji Lee, Seoul (KR); Seong Hee Park, Seoul (KR); Se Chang Kwon, Seoul (KR); Gwan Sun Lee, Seoul (KR)

(73) Assignee: Hanmi Science Co., Ltd., Hwaseong-si (KR)

( * ) Notice: Subject to any disclaimer, the term of this patent is extended or adjusted under 35 U.S.C. 154(b) by 1499 days.

(21) Appl. No.: 12/444,567

(22) PCT Filed: Oct. 16, 2007

(86) PCT No.: PCT/KR2007/005064
§ 371 (c)(1),
(2), (4) Date: Nov. 24, 2009

(87) PCT Pub. No.: WO2008/048037
PCT Pub. Date: Apr. 24, 2008

(65) Prior Publication Data
US 2010/0120089 A1    May 13, 2010

(30) Foreign Application Priority Data
Oct. 16, 2006    (KR) .................. 10-2006-0100507

(51) Int. Cl.
*C07H 21/04*    (2006.01)
*C12N 15/63*    (2006.01)
*C12N 9/06*    (2006.01)
*C12N 15/85*    (2006.01)

(52) U.S. Cl.
CPC ............... *C12N 9/003* (2013.01); *C12N 15/85* (2013.01); *C12N 2510/00* (2013.01)
USPC ..................................... 536/24.1; 435/320.1

(58) Field of Classification Search
CPC ..................... C12N 15/63; C12Q 2525/143
See application file for complete search history.

(56) References Cited

PUBLICATIONS

Farnham et al. Sequences downstream of the transcription initiation site modulate the activity of the murine dihydrofolate reductase promoter. Mol. Cell. Biol. Apr. 1990 vol. 10 No. 4 1390-1398.*
Lin et al. Cloning and expression of the human erythropoietin gene. PNAS 82(22): 7580-7584, 1985.*
Supplemental European Search Report issued in EP 07 83 3373 and completed on Jan. 18, 2010.
Malik, N., et al., "Amplification and Expression of Heterologous Oncostatin M in Chinese Hamster Ovary Cells," DNA and Cell Biology, 11:6, 453-459, Nov. 6, 1992.
Blake, M.C., et al., "Transcription Factor E3F is Required for Efficient Expression of the Hamster Dihydrofolate Reductase Gene In Vitro and In Vivo," Molecular and Cellular Biology, 9:11, 4994-5002, Nov. 1989.
Eastman, H.B., "Stimulation of dihydrofolate reductase promoter activity by antimetabolic drugs," Proc. Natl, Acad, Sci. USA, vol. 88, 8572-8576, Oct. 1991.
Swick, A.G., et al., "Functional analysis of GC element binding and transcription in the hamster dihydrofolate reductase gene promoter," Nucleic Acids Research, 17:22, 9291-9304, Nov. 25, 1989.

* cited by examiner

*Primary Examiner* — Michele K Joike
(74) *Attorney, Agent, or Firm* — Sughrue Mion, PLLC

(57) ABSTRACT

Disclosed herein is an inducible high-expression cassette comprising a dihydrofolate reductase (DHFR) promoter from which GC-rich repeat sequences are partially or entirely removed, the cassette capable of more effectively improving a gene amplification system. Also disclosed are an expression vector comprising the inducible expression cassette and optionally a gene encoding a recombinant protein of interest, an animal cell line transformed with the expression vector, and a method of mass producing and purifying a recombinant protein by culturing the transformant. The present invention enables the shortening of the time required to establish a cell line producing a recombinant protein of interest at high levels using a low concentration of a DHFR inhibitor, thereby allowing more effective production of the recombinant protein.

20 Claims, 8 Drawing Sheets

VECTOR AND EXPRESSION CELL LINE FOR MASS PRODUCTION OF RECOMBINANT PROTEIN AND A PROCESS OF PRODUCING RECOMBINANT PROTEIN USING SAME

This is a national stage application under 35 U.S.C. §371 of PCT/KR2007/005064 filed on Oct. 16, 2007, which claims priority from Korean patent application 10-2006-0100507 filed on Oct. 16, 2006, all of which are incorporated herein by reference.

TECHNICAL FIELD

The present invention relates to a vector for the mass production of a recombinant protein, an expression cell line for producing the recombinant protein, and a method of producing and purifying the recombinant protein using the cell line. More particularly, the present invention relates to a vector capable of greatly enhancing gene amplification efficiency by artificially weakening a dihydrofolate reductase gene promoter, which is a transcriptional control sequence of the gene, an animal cell line transformed with the vector, and a method of expressing a protein of interest using the animal cell line and purifying only a highly glycosylated form of the protein.

BACKGROUND ART

A variety of vectors and hosts have been used for the mass production of recombinant proteins. *E. coli* has been widely used, but has limited usefulness in the production of proteins that need to be glycosylated or have complicated structures. These problems can be overcome using animal cells, yeast cells, transformed animals, transformed plants, and the like.

Yeast is advantageous in the mass production of proteins, but it is well known that yeast glycosylation is different from human glycosylation and is thus highly immunogenic (Hermeling et al., Pharm. Res. 21(6):897-903 (2004)). Transformed animals have not been commercialized owing to difficulty in the care and maintenance of the animals and potential contamination with microbiological pathogens.

The use of animal cell lines is burdened by the high cost of protein production and the time and expense required for cell line establishment, but is most commonly used for recombinant protein production because this system produces a recombinant protein in a form very similar to that seen in human cells and enables stable protein production and maintenance. However, when transformed for recombinant protein production, most animal cell lines exhibit low expression levels and thus have not yet been used to realize high yield production. Gene amplification is a strategy that is routinely used to overcome the problems associated with animal cell expression systems. The two widely used amplification systems are dihydrofolate reductase (DHFR)-based amplification and glutamine synthetase-based amplification, both of which can considerably increase the recombinant protein yield of animal cell lines. Despite its advantage of improving protein production, gene amplification systems have drawbacks in that they require multiple rounds of gene amplification in order to use high concentrations of methotrexate (hereinafter, referred to simply as "MTX"), which are time-consuming, and the long-term subculture of cell lines leads to gene loss and unstable expression.

Many attempts have been made to overcome the drawbacks of gene amplification systems. For example, Korean Pat. Registration No. 0162021 employs a DHFR gene which is placed under the control of a partially deleted SV40 promoter. Korean Pat. Registration No. 0493703 describes the introduction of a mutation into a cytomegalovirus (CMV) promoter so as to alter the affinity of methylated DNA-binding protein to its recognition sequence in the promoter. Korean Pat. Registration No. 0184778 employs the 5'-noncoding region of an immunoglobulin heavy chain binding protein (Bip) as an internal ribosome entry site (IRES) in order to place a DHFR gene under the control not of an independent promoter but of a transcription control sequence of a recombinant protein of interest.

Korean Pat. Registration No. 0162021 was directed to the control of the activity of the SV40 promoter by deleting 128 to 270 nucleotides. However, the role of the deleted sequence is not accurately known, and the role of the remaining sequence is not mentioned. In particular, because this patent does not show that gene amplification is not increased any further at concentrations of MTX higher than 20 nM under a condition not containing a control, it does not provide any support at all for the change in the DHFR promoter activity and the optimized expression at a low concentration of MTX. Korean Pat. Registration No. 0493703 intended to achieve effective gene amplification by modifying the recognition sequence of methylated DNA-binding protein in the CMV promoter, but the amplification effect on expression is lower than that of other methods. In Korean Pat. Registration No. 0184778, the IRES-dependent expression, conducted instead of the use of an independent promoter, allows gene amplification merely at levels of MTX as low as several micromoles (μM), and a roughly 30-fold expression increase. Thus, the amplification of the DHFR gene cannot be predicted from the modification of a general promoter, and the application of a modified promoter will be determined only when gene amplification is substantially performed using various kinds of promoters.

Human erythropoietin (EPO), which is illustrated as an example of recombinant proteins in the present invention, is a glycoprotein of about 34 kDa, but the molecular mass of the peptide chain (non-glycosylated EPO) is only about 18 kDa. EPO is synthesized in the kidney in response to anemia, hypoxia or bleeding, and stimulates the production of red blood cells and maintains homeostasis. EPO is present at about 10 to 20 mIU/mL in adults, and renal dysfunction brings about severe anemia (Jacobson, et al., Nature, 179: 633-634 (1957)). Thus, EPO has been used as a therapeutic agent for chronic renal failure and anemia caused by various factors. In the past, EPO was harvested from the blood plasma of animals, or from the blood or urine of patients having aplastic anemia, who produce EPO at higher levels than healthy persons, but EPO is obtained in an unstable form and in low yield. Urinary EPO from healthy persons is obtained at low concentrations, and needs to be highly purified because urine contains an inhibitor of EPO activity (see, U.S. Pat. Nos. 4,397,840, 4,303,650 and 3,865,810). Since it is difficult to obtain large amounts of highly pure EPO from the blood or the urine, EPO preparation methods using genetic recombination techniques have been developed. However, since glycosylation is required for the in vivo activity of EPO, when an EPO gene is cloned and expressed in *E. coli* or yeast, EPO is not glycosylated in its native form, and thus does not display its biological activity. Hence, the use of a recombinant animal cell line is essentially required for EPO production. In the case of using a recombinant animal cell line, EPO is usually produced based on a DHFR gene amplification system (Malik et al., DNA and Cell Bio., 6:453-459 (1992)).

Disclosure

Technical Problem

Based on a previous study conducted by Michel Fromm and Paul Berg (J. Mol. Appl. Genet. 1983. 2(1):127-135), suggesting that six GC-rich repeating sequences in a promoter region linked to a DHFR structural gene are important for the transcriptional activity of the promoter, the inventors of this application constructed an expression vector for animal cells, which is more effective in gene amplification and expression, by sequentially deleting the GC-rich sequences, thereby leading to the present invention.

Technical Solution

It is therefore an object of the present invention to provide an expression vector which is more effective in gene amplification for the production of a recombinant protein in animal cells.

It is another object of the present invention to provide an animal cell line transformed with the expression vector.

It is a further object of the present invention to provide a method of mass producing a recombinant protein using the animal cell line.

BEST MODE

Figure 1:
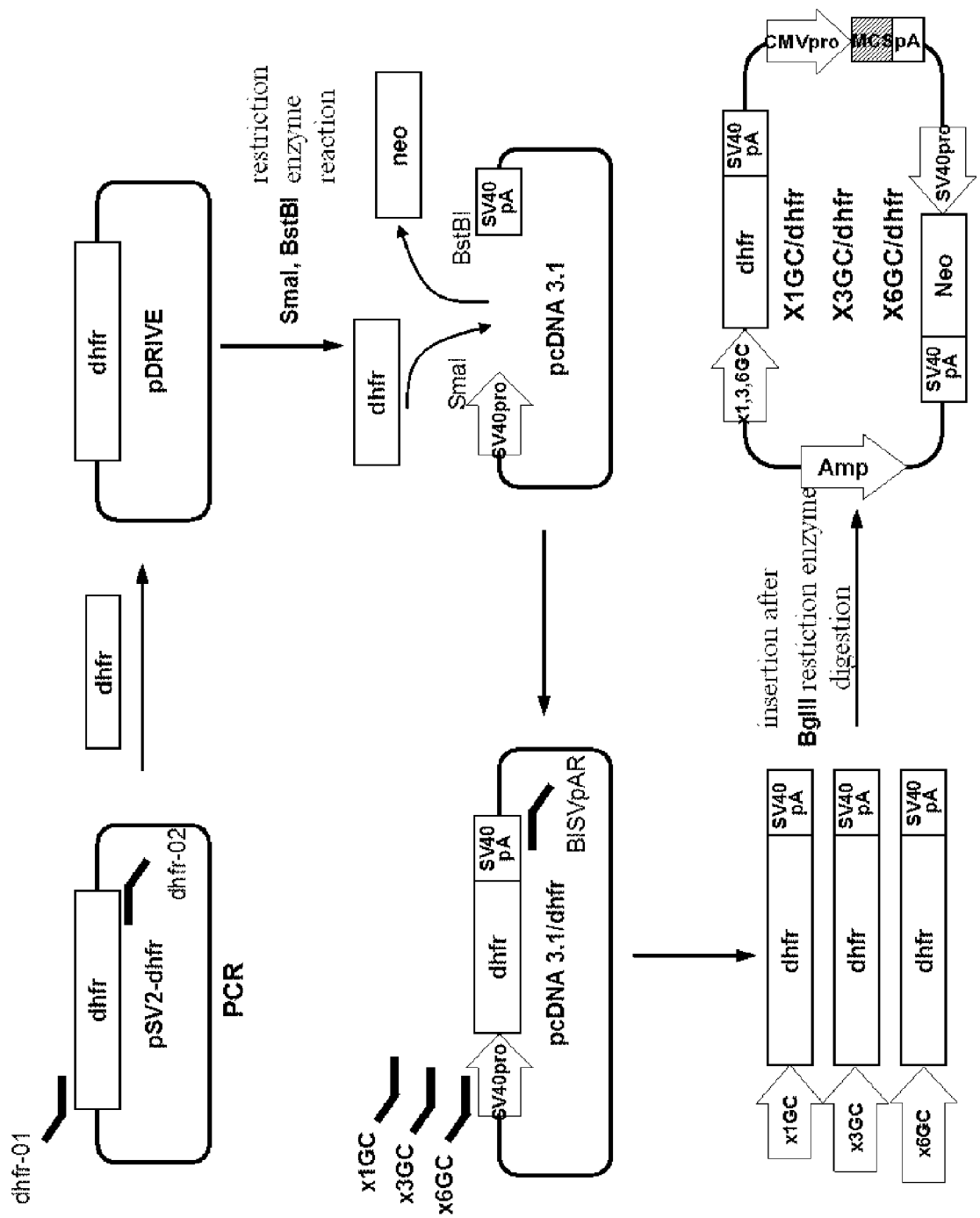
FIG. 1 schematically represents a process of constructing expression vectors X1GC/dhfr, X3GC/dhfr and X6GC/dhfr, which contain full-length or sequentially truncated GC-rich sequences.

In order to accomplish the above objects, the present invention provides an expression vector for an animal cell line comprising a dihydrofolate reductase (DHFR) gene promoter from which some repeating GC-rich sequences have been deleted.

As described above, a DHFR-based gene amplification system has been widely used for inducing high level expression of recombinant proteins in animal cells, but is problematic in that it does not guarantee cell line stabilization and is time-consuming and expensive due to the long-term use of a DHFR inhibitor at a high concentration. The present inventors found that an expression vector harboring a DHFR gene, which is placed under the control of a truncated DHFR promoter from which GC-rich repeat sequences have been partially or entirely deleted, is able to induce the expression of the DHFR gene and/or a recombinant gene of interest, carried therein, at higher efficiency in a shorter time even at a lower concentration of a DHFR inhibitor.

As used herein, the term "GC-rich repeat sequences" refers to the repeated CCGCCC sequences that are contained in a DHFR promoter, which is a transcriptional control sequence of DHFR. When the repeat sequences are partially or entirely rendered inactive by a deletion or other mutations, DHFR expression is minimized. When a DHFR inhibitor is added in a state in which HDFR expression is maintained at minimal levels, cells amplify the larger number of DHFR gene for survival, and as well, a recombinant gene of interest, carried by an expression vector harboring the DHFR gene, is amplified and thus expressed at high levels.

Thus, in one detailed aspect of the present invention, there is provided an inducible expression cassette for high level expression comprising a nucleotide sequence coding for a dihydrofolate reductase (DHFR) gene containing a promoter from which one or more CCGCCC repeat sequences have been removed. The inducible high-expression cassette comprises preferably a DHFR promoter that contains less than six CCGCCC repeat sequences, more preferably a DHFR promoter that contains less than three CCGCCC repeat sequences, particularly preferably a DHFR promoter that contains zero or one CCGCCC repeat sequences, and more particularly preferably a DHFR promoter from which all repeating CCGCCC sequences have been removed.

The removal of the CCGCCC repeat sequences may be achieved through nucleotide substitution, deletion, or the like according to a genetic recombination technique widely known in the art. In the practice of the present invention, the GC-rich sequences are partially or entirely removed from the promoter through partial or entire deletion of a nucleotide sequence containing the CCGCCC sequences.

In another aspect, the present invention provides an expression vector comprising the inducible high-expression cassette.

As used herein, the term "vector" means a vehicle for introducing a gene of interest into a host cell to express the gene. Vectors useful in the present invention include plasmid vectors, cosmid vectors, bacteriophage vectors, and viral vectors such as adenovirus vectors, retrovirus vectors and adeno-associated virus vectors. Plasmid vectors are preferred.

Preferably, the expression vector may further include a gene encoding a recombinant protein of interest. The recombinant protein of interest may be expressed at high levels by expressing the expression vector.

The recombinant protein of interest typically includes physiologically active polypeptides. Such physiologically active polypeptides include a variety of proteins such as hormones, cytokines, interleukins, interleukin binding proteins, enzymes, antibodies, growth factors, transcription regulatory factors, coagulation factors, vaccines, structural proteins, ligand proteins or receptors, cell surface antigens, receptor antagonists, and derivatives and analogues thereof.

In detail, non-limiting examples of the physiologically active polypeptides include human growth hormone, interferons and interferon receptors, colony stimulating factors, interleukins, erythropoietin, insulin, angiotensin, bone growth factor, B cell factor, T cell factor, nerve growth factors, cell surface antigens, monoclonal antibodies, and virus derived vaccine antigens.

Those skilled in the art will readily select a recombinant protein capable of being applied to a DHFR-based gene amplification system using current technology. In the preferred practice of the present invention, the recombinant protein is human erythropoietin.

The recombinant protein of interest may be expressed under the control of the DHFR gene promoter or under the control of an independent promoter. Preferably, the recombinant protein of interest may be placed under the control of an independent promoter. Such promoters include those widely known in the art, and non-limiting examples of such promoters include cytomegalovirus (CMV) promoter, LTR promoter, EFα promoter, SV40 promoter and TK promoter. Those skilled in the art will readily select any one from the group consisting of the aforementioned promoters.

The expression vector of the present invention, which is provided for inducing high expression of a gene of interest in animal cells, may preferably further include a resistance gene for animal cells, which is used as a selectable marker for permanent expression of the gene in animal cells. Non-limiting examples of such resistance genes for animal cells include those commonly used in the art, such as the neomycin resistance gene, the zeomycin resistance gene, the hygromycin resistance gene, and the blastomycin resistance gene.

As well, the expression vector of the present invention may further include, but is not limited to, general constituent elements of a vector, such as a replication origin and a polyadenylation signal, and other transcriptional control elements.

In a further aspect, the present invention provides a cell line transformed with the expression vector.

In a detailed aspect, the present invention provides E. coli cell lines which are transformed with an expression vector harboring an inducible high-expression cassette containing one CCGCCC repeat sequence in the DHFR promoter and another inducible high-expression cassette not containing any CCGCCC sequence. The E. coli transformants were deposited at an international depositary authority, KCTC (Korean Collection for Type Cultures; Genetic Resources Center, Korean Research Institute of Bioscience and Biotechnology (KRIBB), Yusong-ku, Taejon, Korea) on Oct. 2, 2006, and assigned accession numbers KCTC 10991 BP and KCTC 10992 BP, respectively. In order to induce the high expression of a recombinant protein of interest, the E. coli cell lines may be used for constructing an expression vector further including a gene encoding the recombinant protein of interest through a cloning procedure into the inducible high-expression cassette-containing expression vector, isolated from the cell lines, using a gene recombination technique.

In another detailed aspect, the present invention provides a cell line transformed with the expression vector, which further includes a gene encoding a recombinant protein of interest.

In a preferred aspect, the recombinant protein of interest needs to be expressed in animal cells. With respect to the purpose of the present invention, examples of animal cells suitable for use in the present invention include, but are not limited to, Chinese hamster ovarian carcinoma (CHO) cells, monkey kidney cells (COS 7), NSO cells, SP2/0 cells, W138 cells, baby hamster kidney (BHK) cells, MDCK cells, myeloma cells, HuT 78 cells, and 293 cells. Those skilled in the art can easily select an animal cell line suitable for use in the DHFR-based amplification system according to the present invention.

In practice, CHO cells were used. In detail, a dihydrofolate reductase (DHFR)-deficient Chinese hamster ovarian carcinoma cell line (CHO/dhfr-) was used. That is, DHFR-deficient CHO cells were transformed with an expression vector carrying a gene encoding recombinant human erythropoietin according to the present invention. In the transformed CHO cells, the gene was found to be amplified to a sufficient number of copies even at a methotrexate concentration less than 100 nM, and even less than 50 nM, which was preferable. Thus, the present invention provides such an animal cell line. The CHO transformants, which will be described in detail in Examples, were deposited at the KCTC (Genetic Resources Center, KRIBB, Yusong-ku, Taejon, Korea) on Oct. 2, 2006, and assigned accession numbers KCTC 10993BP, KCTC 10994BP and KCTC 10995BP.

In yet another aspect, the present invention provides a method of producing a recombinant protein comprising transforming an animal cell line with the expression vector for animal cells according to the present invention, including a gene encoding dihydrofolate reductase (DHFR) containing a promoter from which GC-rich sequences have been partially or entirely removed and a gene encoding recombinant protein; and culturing the transformed animal cell line.

In the present invention, "transformation" into animal cells includes any methods by which nucleic acids can be introduced into organisms, cells, tissues or organs, and, as known in the art, may be performed by selecting suitable standard techniques according to animal cell lines. Mammalian cells not having cell walls may be transformed using calcium phosphate precipitation (Graham et al., 1978, Virology, 52:456-457). General methods and features for transformation into mammalian host cells are described in U.S. Pat. No. 4,399,216. In detail, a vector expressing a recombinant protein was introduced into CHO cells using lipofectamine. The animal cells may be cultured in a suitable medium and under suitable culture conditions, which are known in the art. The culture conditions may be readily adjusted by those skilled in the art to be suitable for selected animal cell lines. Culture may be performed in a suspension or in an adherent state according to the growth traits of cells according to any of batch culture, bed-batch culture and continuous culture. The medium used for culture should satisfy the growth requirements of specific cell lines.

The medium used in animal cell culture contains a variety of carbon sources, nitrogen sources and trace elements. Examples of available carbon sources include carbohydrates such as glucose, sucrose, lactose, fructose, maltose, starch and cellulose, fats such as soybean oil, sunflower oil, castor oil and coconut oil, fatty acids such as palmitic acid, stearic acid and linoleic acid, alcohols such as glycerol and ethanol, and organic acids such as acetic acid. These carbon sources may be used singly or in combinations of two or more. Examples of available nitrogen sources include organic nitrogen sources, such as peptone, yeast extract, meat extract, malt extract, corn steep liquor (CSL) and soybean whey, and inorganic nitrogen sources, such as urea, ammonium sulfate, ammonium chloride, ammonium phosphate, ammonium carbonate and ammonium nitrate. These nitrogen sources may be used singly or in combinations of two or more. The medium may further include amino acids, vitamins, suitable precursors, and the like.

As well, the medium may be supplemented with a DHFR inhibitor, such as methotrexate. This is because, as described above, the present invention aims to effectively establish in a short time a system by which a DHFR gene carried in a vector is amplified and selected by transforming DHFR-deficient animal cells with an expression vector according to the present invention and dosing the cells with a DHFR inhibitor in order to amplify a recombinant gene.

In a preferred embodiment, a DHFR inhibitor is preferably used at a concentration as low as possible for a short period of time with respect to the stability of cell lines and production cost. That is, the use of a DHFR inhibitor at a low concentration ensures the stable mass production of a protein of interest and shortens the time required for the development of an expression cell line. In detail, the present invention provides a method of producing a recombinant protein by transforming DHFR-deficient CHO cells with the recombinant protein expression vector and dosing the cells with less than 100 nM methotrexate, and preferably less than 50 nM methotrexate.

When erythropoietin is produced in the aforementioned cell line, the method may further include purifying at a large scale erythropoietin having high sialic acid content, which confers enhanced biological activity to erythropoietin.

In an embodiment of the present invention, GC-rich sequences contained in the DHFR promoter were rendered inactive so as to minimize DHFR expression, and the DHFR gene was then amplified through the addition of a DHFR inhibitor. Transformed cells in which gene amplification occurs were subjected to limiting dilution in order to obtain clonal populations derived from single cells. The single-cell clones thus obtained were cultured in a serum-free medium on a large scale in order to produce recombinant human erythropoietin. Based on the fact that erythropoietin (EPO) having high sialic acid content is eluted at a low salt concentration contain and that EPO having a low sialic acid content is eluted at a high salt concentration, the produced EPO was applied onto a column and eluted from the column with an increasing salt gradient. The activity of the purified EPO, which had high sialic acid content, was found to be intact.

MODE FOR INVENTION

A better understanding of the present invention may be obtained through the following examples which are set forth to illustrate, but are not to be construed as the limit of the present invention.

Example 1

Construction of Expression Vectors Containing Full-Length or Truncated GC-Rich Sequences DHFR gene expression cassettes were prepared so as to place a DHFR gene under the control of a truncated promoter from which some GC-rich repeat sequences had been deleted, as follows. In order to amplify a DHFR gene, PCR was carried out using a pSV2-dhfr plasmid (ATCC No. 37146) with a pair of primers: dhfr 01 primer having a SmaI site (5'-GCG CCC GGG ATG GTT CGA CCA TTG AAC TGC-3', SEQ ID NO. 11) and dhfr-02 primer having a BstBI site (5'-CAC TTA GAA CCT GTT AGT CTT TCT TCT CGT AGA C-3', SEQ ID NO. 12). A PCR product of about 200 bp was electrophoresed on a 1% agarose gel and purified using a gel extraction kit (QIAGEN Cat No. 28706). The DNA fragment was cloned into a pDRIVE vector (Qiagen) and subjected to DNA sequencing. The DNA sequencing revealed that the amplified DHFR gene had no errors. Then, the pDRIVE-dhfr plasmid was digested with SmaI and BstBI to excise the DHFR gene, and electrophoresed on a 1.5% agarose gel. A DHFR gene fragment of about 200 bp was purified using a gel extraction kit (QIAGEN Cat No. 28706) and inserted into pcDNA 3.1 (Invitrogen), which was predigested with the same restriction enzymes. Using the resulting pcDNA3.1-dhfr plasmid as a template, PCR was performed in a state in which primers that had a BamHI site and were complementary to different GC-rich repeat sequences, x 1GC (5'-TCA GGA TCC ATT CTC CGC CCC ATG GCT GAC TAA-3', SEQ ID NO. 13), x 3GC (5'-CAT GGA TCC TAA CTC CGC CCA GTT CCG CCC ATT CT-3', SEQ ID NO. 14) and x 6GC (5'-CAT GGA TCC CAT AGT CCC GCC CCT AAC TCC GCC C-3', SEQ ID NO. 15); and a primer that had a BamHI site and was complementary to a polyadenylation signal sequence structurally linked to the DHFR gene, BISVpAR (5'-TCA GGA TCC CAG ACA TGA TAA GAT ACA TTG ATG-3', SEQ ID NO.

18) in order to obtain two gene cassettes containing partially truncated GC-rich sequences and one gene cassette containing full-length GC-rich sequences. Then, the gene cassettes were inserted into pcDNA 3.1 (Invitrogen), which was pre-digested with BglII. Clones having the same orientation as the CMV promoter of the vector were selected using restriction mapping, thereby obtaining X1GC/dhfr, X3GC/dhfr and X6GC/dhfr plasmids. An erythropoietin gene was obtained from human genomic DNA and cloned into each of the plasmids. In addition, as a control, an expression vector containing a DHFR promoter from which all GC-rich sequences had been deleted was constructed as follows.

In order to obtain a DHFR gene and an SV40 viral polyadenylation sequence, primers containing a BamHI site, X0GC (5'-CGA TGG ATC CGA CAT GAT AAG ATA CAT TGA T-3', SEQ ID NO. 16) and X0GCRR (5'-CGT TGG ATC CAC AGC TCA GGG CTG CGA TTT C-3', SEQ ID NO. 17), were synthesized. PCR was carried out using pSV2-dhfr as a template with the primers. A PCR product of 1.5 kb, spanning from the SV40 viral polyadenylation sequence to the 5'-non-coding region of the DHFR gene, was obtained. The amplified DNA fragment was electrophoresed on a 1% agarose gel, purified using a gel extraction kit (QIAGEN Cat No. 28706), and inserted into pcDNA 3.1 (Invitrogen), which was predigested with BglII. A clone in which the DHFR gene had orientation opposite to that of the CMV promoter was selected using restriction mapping. The multicloning site of the vector was digested with NdeI and DraIII in order to remove some restriction enzyme recognition sites, and the excised gene fragment was inserted into pRcCMV (Invitrogen) and predigested with the same restriction enzymes, thereby obtaining a X0GC/dhfr vector.

Figure 2:
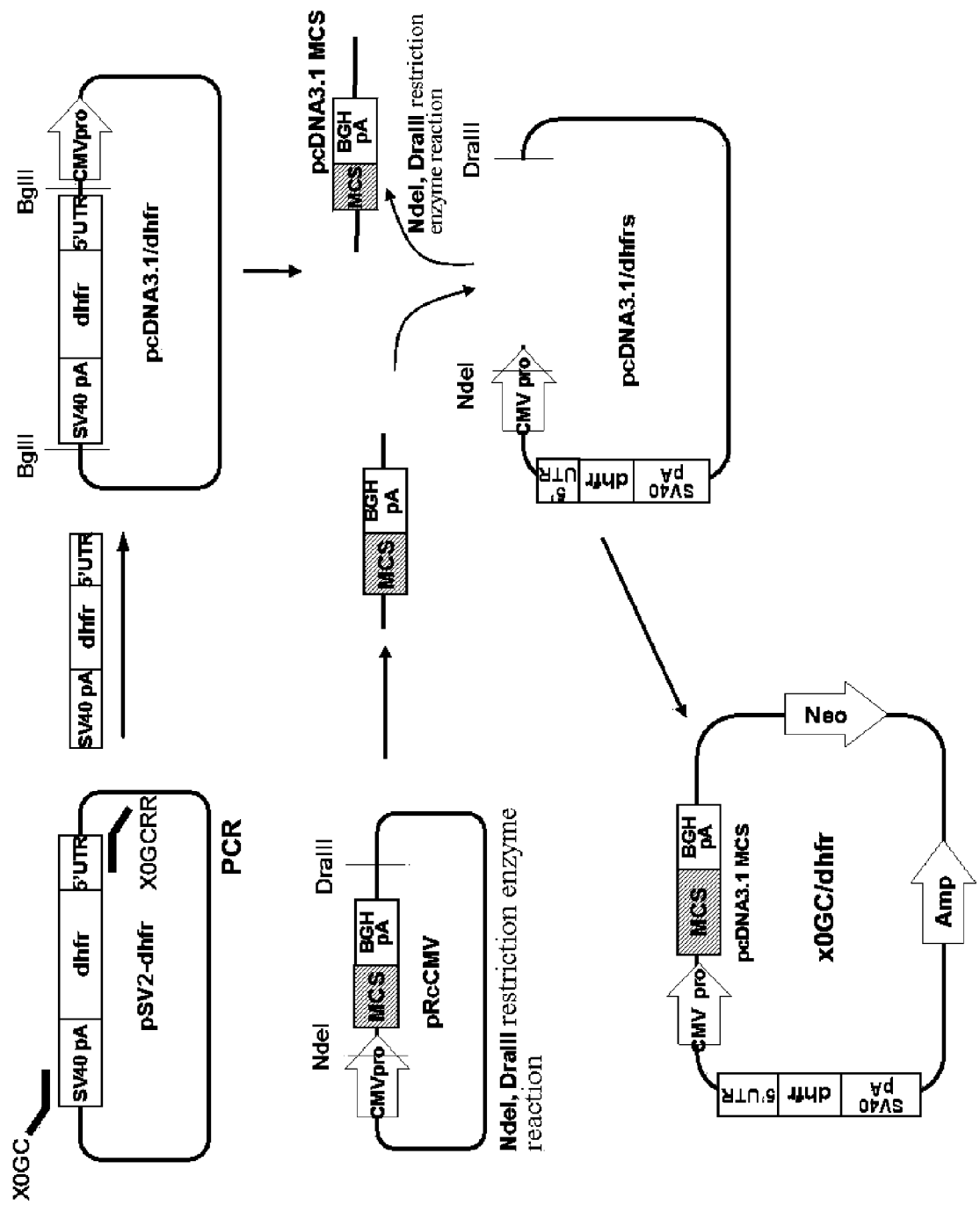
FIG. 2 schematically represents a process of constructing an X0GC/dhfr expression vector, from which all of six GC-rich sequences have been deleted.

The cloning procedures are schematically shown in FIGS. 1 and 2.

Example 2

Cloning of gEPO Gene

Figure 3:
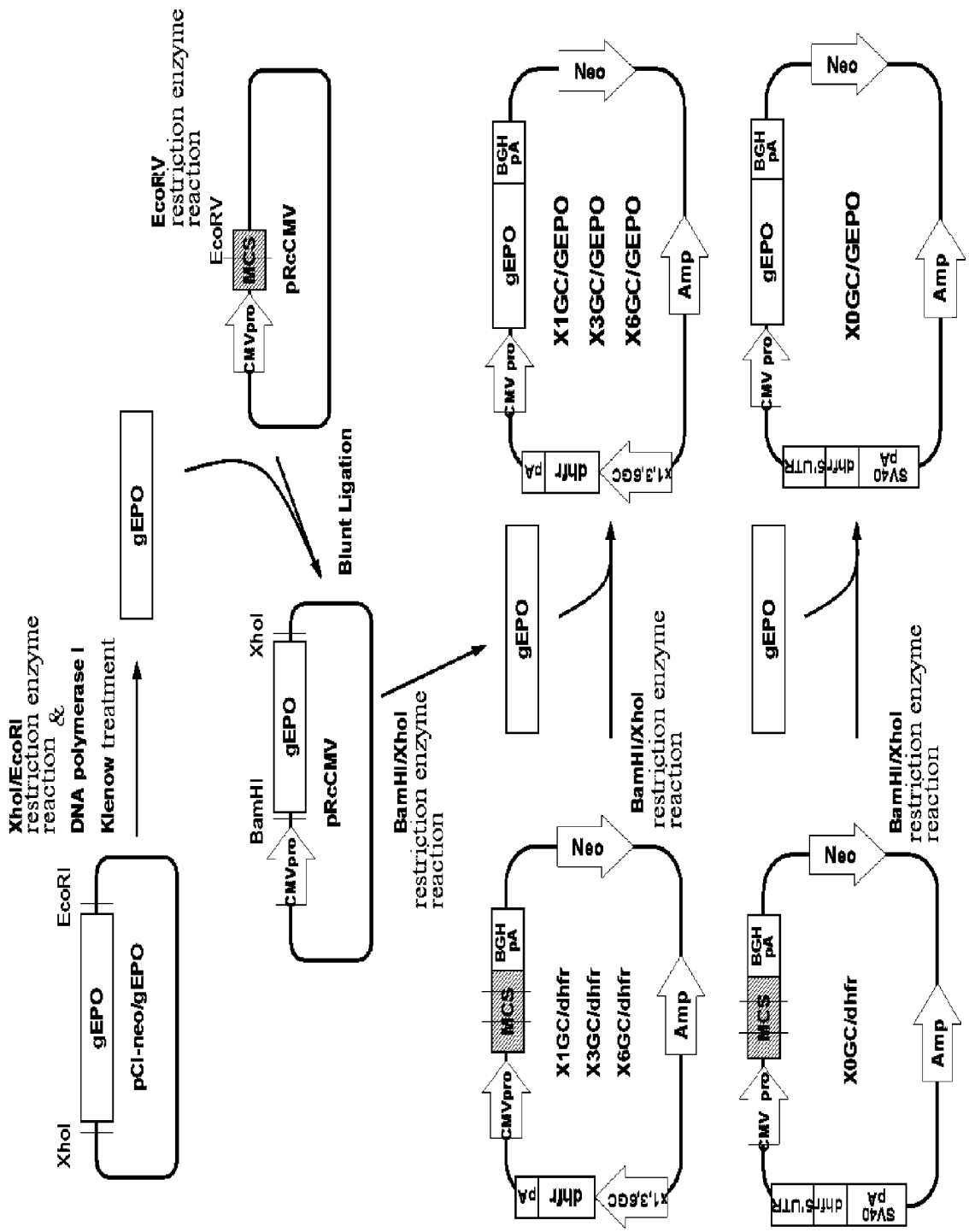
FIG. 3 schematically represents a process of cloning a gEPO gene into the expression vectors of FIGS. 1 and 2.
Figure 4:
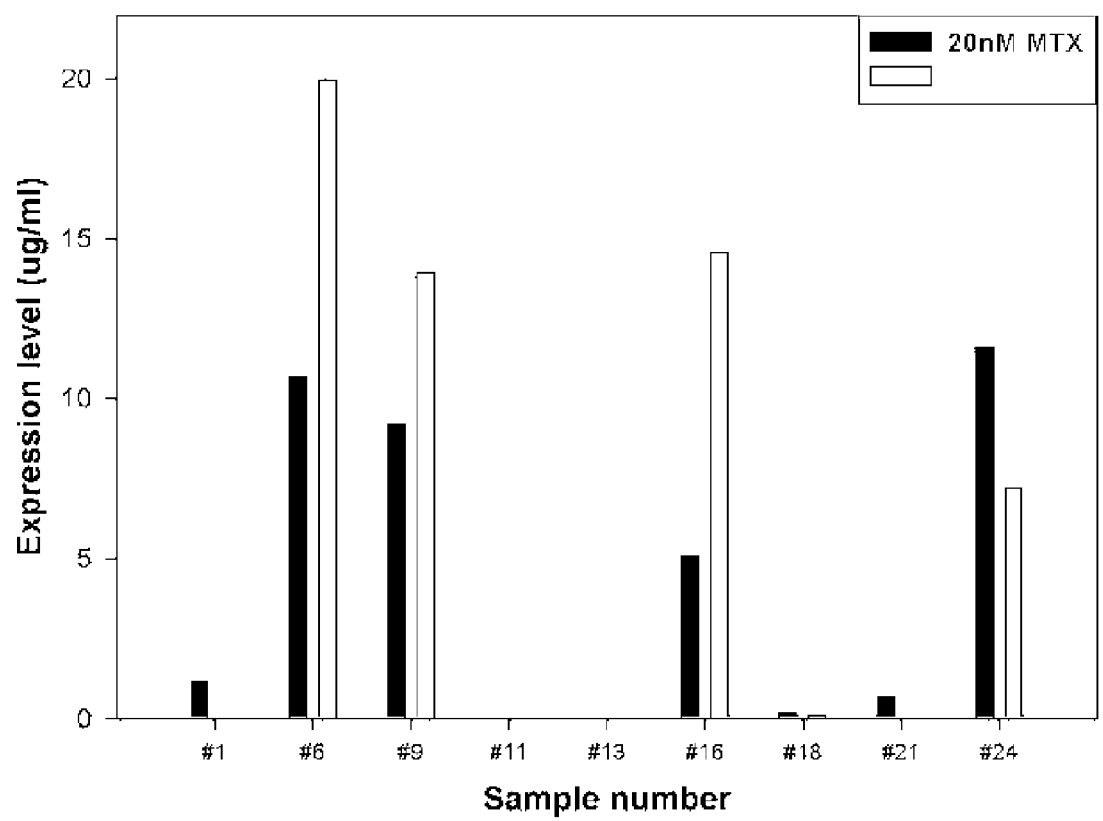
FIGS. 4 to 7 show the results of ELISA analysis for EPO expression levels of cell lines each transformed with an expression vector according to the present invention.
Figure 5:
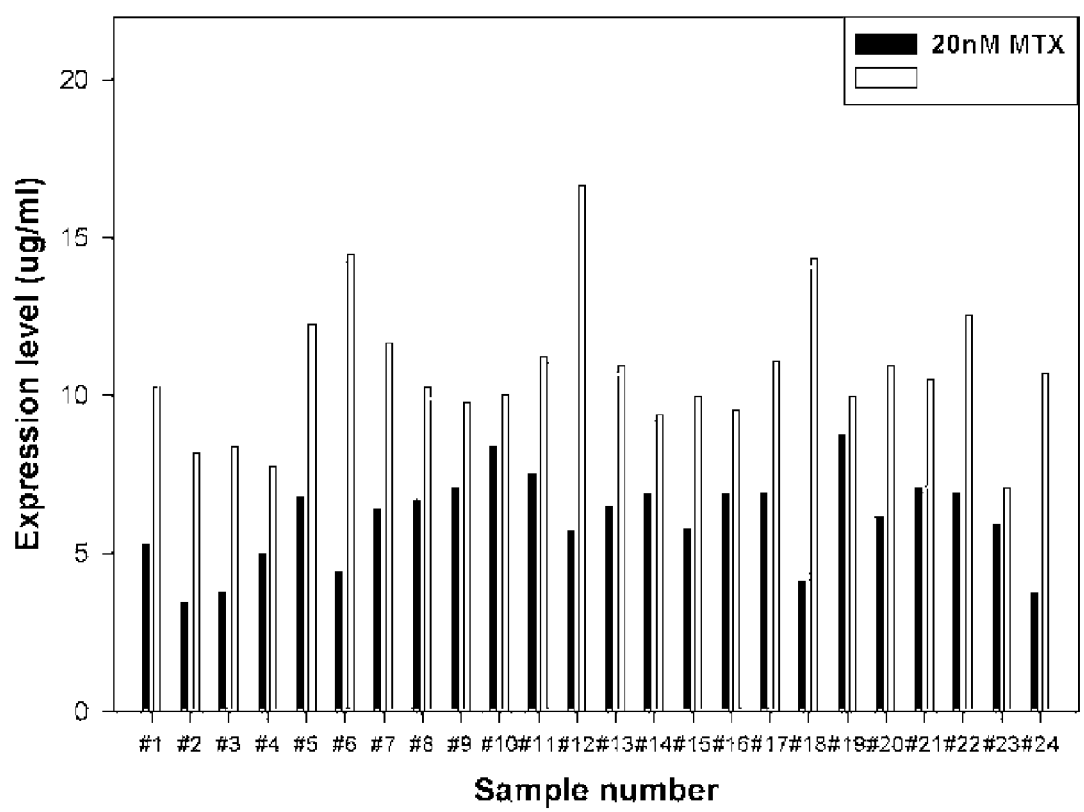
Figure 6:
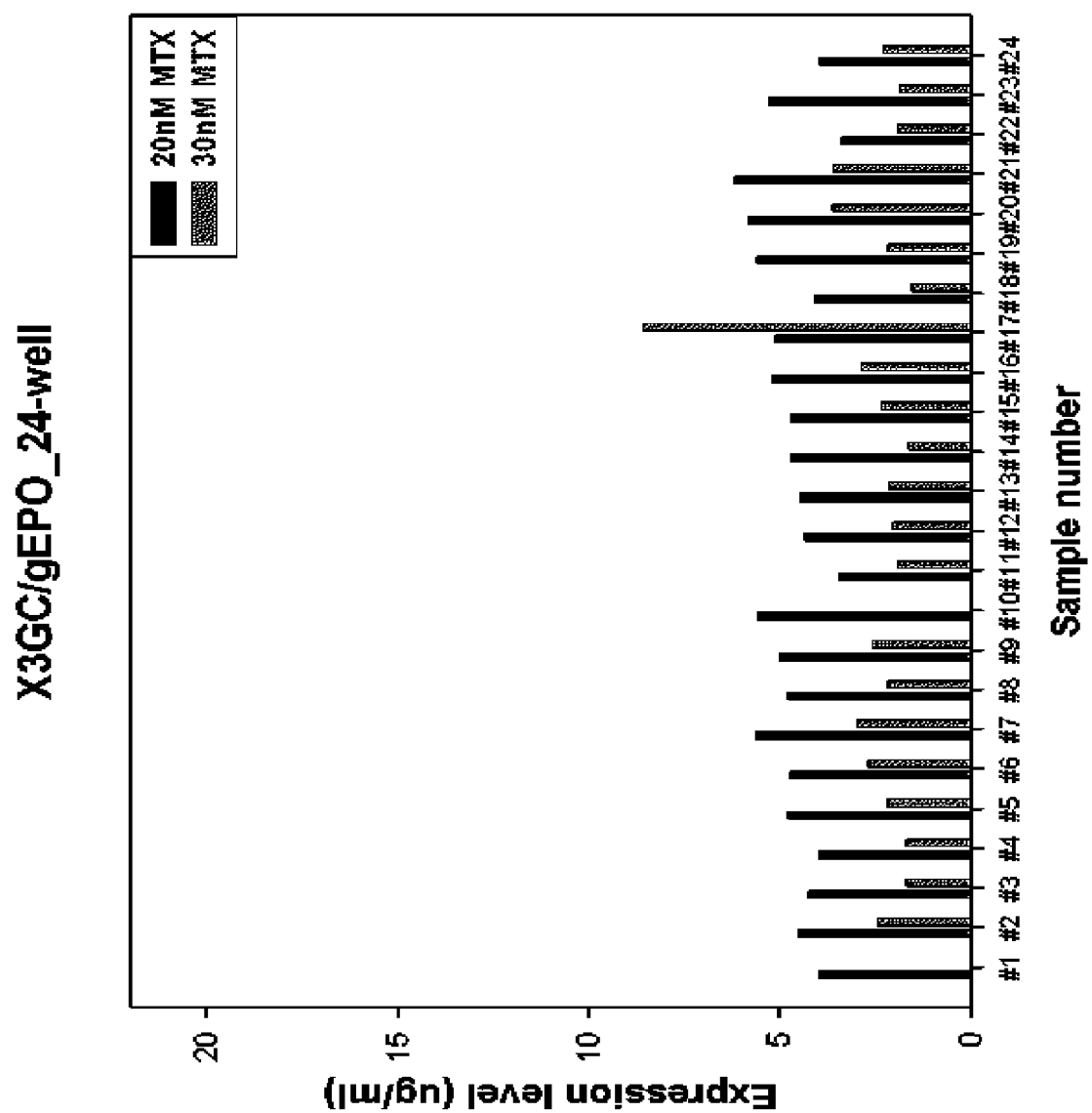
Figure 7:
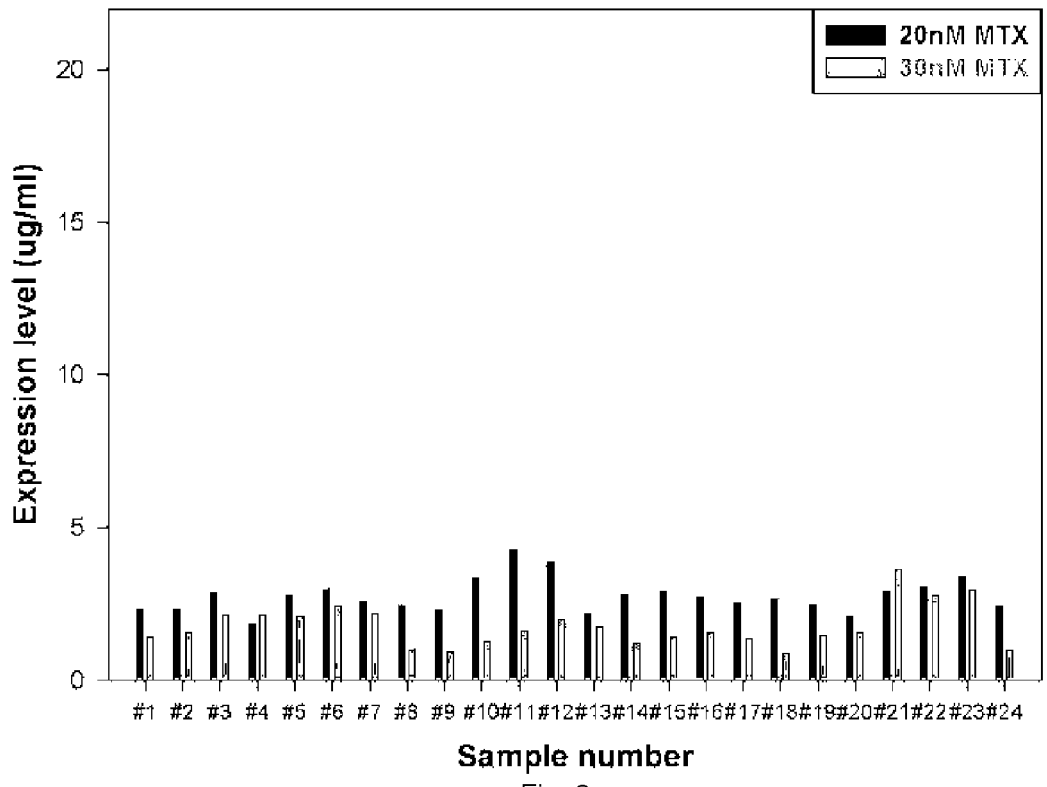
Figure 8:
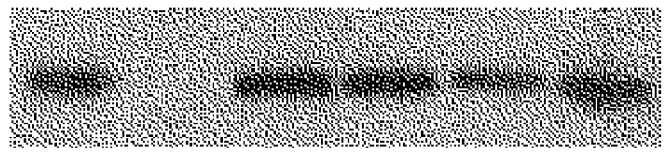
FIG. 8 shows the results of Western blotting for expression levels of an amplified DHFR gene.

A pCI-neo/gEPO plasmid was digested with XhoI and EcoRI, filled in with a Klenow fragment of DNA polymerase I at its cohesive ends to generate blunt ends, and electrophoresed on a 0.7% agarose gel. A DNA fragment of about 2.2 kb, corresponding to the genomic human EPO gene, was purified using a gel extraction kit (QIAGEN, Cat No. 28706). A pRc-CMV vector (Invitrogen) was digested with EcoRV and purified using a PCR purification kit (QIAGEN, Cat No. 28106). The genomic EPO gene was ligated to the EcoRV site of the vector. A clone in which the EPO gene had the same orientation as the CMV promoter was selected using restriction mapping. The X0GC/dhfr, x1GC/dhfr, x3GC/dhfr and x6GC/dhfr vectors prepared in Example 1 were digested with BamHI and XhoI, electrophoresed on a 0.7% agarose gel, and purified using a gel extraction kit (QIAGEN, Cat No. 28706). According to the same method, the genomic EPO gene fragment, cloned into pRcCMV, was purified and inserted into BamHI/XhoI sites of the multicloning site of the x0GC/dhfr, x1GC/dhfr, x3GC/dhfr and x6GC/dhfr vectors. The thus obtained vectors were confirmed to have no errors through DNA sequencing, and were designated X0GC/GEPO, X1GC/GEPO, X3GC/GEPO and X6GC/GEPO, respectively. The cloning procedure is schematically shown in FIG. 3, and each final nucleotide sequence is shown in the accompanying sequence listing.

Example 3

Transformation of DHFR-Deficient CHO Cells

DHFR-deficient CHO cells (CHO/DXB11 and CHO/DG44 strains) were subcultured in DMEM/F12 medium (Welgene, Cat No. LM002-04) supplemented with 10% fetal bovine serum (Welgene, Cat No. S101-01) and 1% penicillin-streptomycin (Gibco, Cat No. 15140-122) in a 5% $CO_2$ incubator at 37° C. In order to transform DHFR-deficient CHO cells with the X0GC/GEPO, X1GC/GEPO, X3GC/GEPO and X6GC/GEPO plasmids, 1×10⁶ cells were seeded onto 6-cm culture dishes, cultured for 24 hrs in a 5% $CO_2$ incubator at 37° C., and washed with Opti-MEM medium (Gibco, Cat No. 31985-070) twice. 1 ml of Lipofectamine™ Reagent (Invitrogen, Cat No. 18324-020) was mixed with 10 μg of each plasmid DNA in 1 ml of Opti-MEM, and allowed to stand at room temperature for 20 min. The DNA-lipofectamine complexes were dropped onto the prepared DHFR-deficient CHO cells, and cells were cultured for 18 hrs in a 5% CO2 incubator at 37° C. Then, the medium was exchanged with DMEM/F12 medium supplemented with 10% FBS and 1% penicillin-streptomycin, and cells were further cultured for 48 hrs. In order to select transformed cells, cells were treated with 0.5% Trypsin-EDTA (Gibco., Cat. No. 15400-054), harvested through centrifugation, and seeded onto a T 25 culture flask containing α-MEM selection medium (Welgene, Cat No. LM008-02), supplemented with 10% dialyzed FBS (Welgene) and 1% penicillin-streptomycin and 800 μg/ml of Geneticin (Mediatech, Cat No. 61-234 RG). The cells were allowed to grow in a 5% $CO_2$ incubator at 37° C. until they reached more than 90% confluency. The selection of transformed cells was continued using the same concentration of Geneticin and under the same culture conditions. When a larger number of GC-rich repeat sequences were deleted, the transformed cells were selected faster. No significant difference was observed between the DHFR-deficient CHO strains.

Example 4

Selection of Recombinant Cell Lines and Amplification of EPO Gene

*65In order to increase the expression levels of EPO in the transformed cells (CHO/DXB11 strain or CHO/DG44 strain) selected using Geneticin, 2×104 cells were seeded onto a 24-well plate containing the same selection medium as described above, supplemented with 20 nM of methotrexate (MTX, Sigma, Cat No. M-8407), and cultured for two weeks in a 5% CO2 incubator at 37° C. In order to select transformed cells expressing EPO at high levels, when cells reached 100% confluency, they were washed with PBS (Welgene, Cat No. LB 001-02) twice, and 200 μl of an EPO production medium, CHO-A-SFM (Gibco. Cat No. 05-5072EF), was added to each well. After cells were cultured for 24 hrs, culture supernatants were collected and analyzed using an EPO ELISA kit (R&D systems, Cat No. DEP00). In addition, the transformed cells were cultured for two weeks in the selection medium supplemented with 30 nM of MTX, and EPO expression levels of transformed cells were measured using an ELISA (enzyme linked immunosorbent assay) kit (R&D systems, Cat No. DEP00). As shown in FIGS. 4 to 7, X0GC/GEPO and X1GC/GEPO plasmids displayed the highest EPO expression levels at the same MTX concentrations, followed by X3GC/GEPO and X6GC/GEPO. These results indicate that the removal of a larger number of GC-rich repeat sequences increases gene amplification at the same MTX concentration. Also, X0GC/GEPO, from which all GC-rich repeat sequences were removed, was found to be effective in gene amplification. Thus, gene amplification was found to be maximized when GC-rich repeat sequences were present in a minimal number. In addition, when the MTX concentration was increased to 40 nM to 60 nM in the selection medium in order to determine the MTX concentration that maximized gene expression, no significant increase in gene expression or acidic isomer content was observed. Based on these results, two CHO strains transformed with X0GC/GEPO and X1GC/GEPO were subjected to limiting dilution, as described in Example 6.

Example 5

Evaluation of DHFR Gene Amplification

The transformed cells obtained in Example 4 were washed with D-PBS once, detached from a culture flask using trypsin-EDTA, and centrifuged for 3 min at 1,000 rpm. The harvested cells were washed with D-PBS once and counted using a hemacytometer (Incyto). After 3×106 cells were centrifuged, the cell pellet was suspended in 1.5 ml of cell lysis buffer (PBS, 5 mM EDTA, 1% NP-40), disrupted at 4° C. for 30 min, and centrifuged at 12,000 rpm for 10 min to obtain the supernatant.

Figure 9:
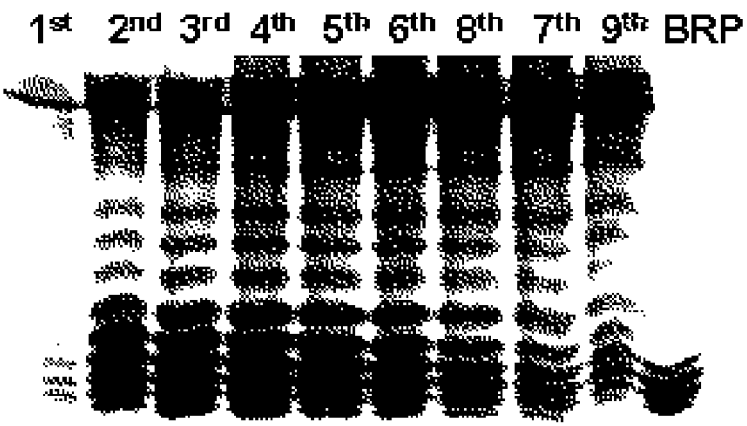
FIG. 9 shows the results of indirect ELISA analysis for expression levels of human EPO in supernatant specimens, which were collected nine times during large-scale culturing of a single-cell clone X0GC/GEPO9647 (DXB11), which is selected in Example 6.

20 μl of each cell lysate and a CHO/dhfr-cell lysate, as a negative control, was mixed with 10 μl of sample buffer, boiled at 100° C. for 5 min, and loaded onto a 12.5% SDS-PAGE gel. As a positive control, 20 ng to 100 ng of dihydrofolate reductase (Sigma, Cat No. D6566) was mixed with sample buffer and loaded onto the SDS-PAGE gel. The gel was electrophoresed at 30 mA. The gel was then placed onto a PVDF membrane and sandwiched between Whatman 3M filter papers. Proteins were transferred onto the PVDF membrane for one hour at 90 mA using a Hoefer Semi-Phor Semi-Dry transfer unit. The blot was then probed with anti-DHFR mouse antibody (1:500 diluted, BD Biosciences, Cat No. 610697) in 10 ml of 0.5% skim milk-containing TBS-T for 1 hr with gentle agitation. The blot was washed with TBS-T five times for 10 min each, and was incubated with horseradish peroxidase-conjugated anti-mouse antibody (diluted 1:3000, Amersham Biosciences, Cat No. RPN2108) in 10 ml of 0.5% skim milk-containing TBS-T for 1 hr with gentle agitation. After the blot was washed with TBS-T five times for 10 min each, Detection Reagents 1 and 2 of an ECL Western Blotting Analysis System (Amersham Biosciences, Cat No. RPN2108) were mixed at a 1:1 ratio, added to the blot, and allowed to react for 1 min. The blot was exposed to an X-ray film, and the film was developed. The results of Western blotting are shown in FIG. 9. As shown in FIG. 9, transformed cells exhibited increased DHFR gene expression. Cells transformed with X0GC/GEPO and X1GC/GEPO displayed higher DHFR expression at the same cell density.

Example 6

Isolation and Selection of Single-Cell Clones

X0GC/GEPO- and X1GC/GEPO-transformed cells, found to have the highest EPO expression in Example 4, were transferred onto 6-well culture plates. In order to isolate single-cell clones, limiting dilution was performed to reach a density of 0.5 cells per well of a 96-well plate using the selection medium supplemented with methotrexate, and the cells were seeded onto the plate. The 96-well plate was incubated for about two or three weeks in a 5% $CO_2$ incubator at 37° C. Wells containing single colonies were selected, and single colonies were transferred onto 24-well plates and allowed to grow. EPO expression levels were measured using indirect ELISA as described in Example 4.

Finally, X0GC/GEPO9647 (DXB11), X1GC/GEPO9629 (DG44) and X0GC/GEPO9603 clones, which showed high expression levels and a high acidic isomer ratio relative to isoelectric focusing dimers, were isolated as single-cell clones, and then assayed for expression levels and isoelectric focusing dimer patterns.

The X0GC/GEPO9647 (DXB11) clone was found to have an expression level of about 80 μg/10E6 cell/day. These results indicate that X0GC/GEPO or X1GC/GEPO enables the establishment of a high expression cell line only through two-step gene amplification, thereby facilitating the establishment of a single-cell clone for protein production with low passage culture.

Example 7

Large-Scale Culture of Single-Cell Clone

Figure 10:
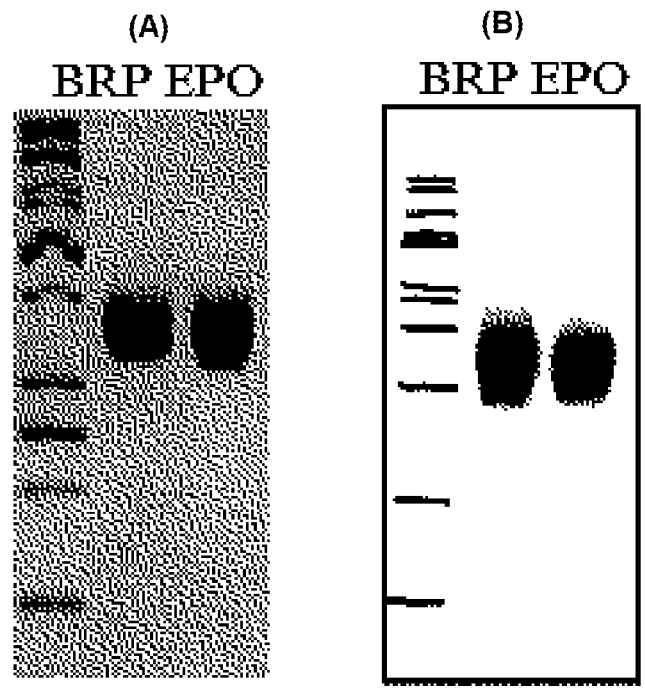
FIG. 10(A) and 10(B) show the results of SDS-PAGE and Western blot analysis, respectively, of recombinant EPO purified in Example 8.

In order to mass produce human EPO, the X0GC/GEPO9647 (DXB11) clone, among the single-cell clones selected in Example 6, was subcultured in one T-175 flask, and expanded stepwise to 120 T-175 flasks. Eight Cell Factories (Nunc, Cat No. 170009) were seeded with about 2.5× 108 cells per Cell Factory, and incubated in a 5% $CO_2$ incubator at 37° C. for about 48 hrs. After each Cell Factory was washed with 1 L of phosphate buffer twice, cells were refed with 1 L of an EPO mass production medium CHO-A-SFM (Gibco, Formula No. 05-5072EF), supplemented with 0.3 mM of sodium butyrate (Sigma, Cat No. B-5887), and cultured in a 5% $CO_2$ incubator at 33° C. Culture supernatants containing expressed EPO were collected nine times every two days. Suspended solids including cell debris were removed from the culture supernatants using a centrifuge and a 0.2-μm filter. The culture supernatants were then assayed for EPO expression levels using indirect ELISA and acidic isoelectric focusing dimer content using isoelectric focusing. As shown in FIG. 10, the clone was found to express EPO at a high level of 40-50 mg/L even upon large-scale culture. The expressed EPO was found to have high content of isomer Nos. 6 to 8, which are an indicator for high sialic acid content, despite not having been subjected to a purification process.

Example 8

Isolation and Purification of Human EPO Having High Sialic Acid Content

The cell supernatants prepared in Example 7 were centrifuged at 7,000 rpm using a Beckman XL-90 centrifuge equipped with a MA-8.1000 rotor in order to remove suspended substances. The centrifugation supernatant was recovered and passed through a 0.2-μm filter and then through an ultrafiltration membrane in order to concentrate it a ⅒ volume. The concentrate was mixed with an equal volume of 20 mM sodium phosphate (pH 7.4), and loaded onto a Blue FF column (Amersham), which was pre-equilibrated with 20 mM sodium phosphate (pH 7.4). The column was washed with five column volumes of 20 mM sodium phosphate (pH 7.4). EPO was eluted from the column with two column volumes of a linear gradient of buffer B (20 mM sodium phosphate, pH 7.4) plus 2 M NaCl.

Major fractions containing EPO were pooled, desalted on a Sephadex G-25 column in 20 mM sodium phosphate, pH 5.4, and loaded onto a SP HP column (Amersham), pre-equilibrated with 20 mM sodium phosphate, pH 5.4. The column was washed with five column volumes of 20 mM sodium phosphate, pH 5.4. EPO was eluted from the column with twelve column volumes of a linear gradient of buffer B (20 mM sodium phosphate, pH 7.4) plus 1 M NaCl. Based on the fact that EPO having high sialic acid content is eluted at a low salt concentration, and that EPO having low sialic acid content is eluted at a high salt concentration, fractions eluted with high salt concentrations, accounting for 30% of total fractions, were excluded, and the remaining fractions were collected. The purified EPO fractions using the SP HP column were pooled, desalted on a Sephardex G25 column in 10 mM Tris, pH 7.5, and loaded onto a Source 15 Q column (Amersham) pre-equilibrated with 10 mM Tris, pH 7.5. EPO was eluted from the column with six column volumes of a linear gradient of buffer B (10 mM Tris, pH 7.5) plus 0.25 M NaCl. More than fifteen fractions containing EPO were collected. Each fraction was analyzed using SDS-PAGE, isoelectric focusing and capillary zone electrophoresis (CZE) for charged isomer distribution. Fractions containing EPO having ten sialic acid moieties and not containing impurities to high salt fractions were finally pooled. Through the purification procedure, recombinant human EPO containing more than ten moles of sialic acid was produced at a yield of about 20 μg/ml.

Example 9

Evaluation of Properties of EPO

1) SDS-PAGE and Western Blotting

The recombinant EPO purified in Example 8 was electrophoresed on two 12% SDS-PAGE gels. One gel was stained with Coomassie Brilliant Blue and destained. The other gel was placed onto a PVDF membrane (Roche) using a Semi-Dry transfer unit. The blot was then probed with an anti-EPO human antibody (1:5,000 diluted, R&D systems, Cat No. AB-286-NA). The blot was washed and incubated with alkaline phosphatase-conjugated anti-mouse rabbit antibody (Amersham, Cat No. NA934V). The blot was sufficiently washed with 0.5% Tween 20 in phosphate buffer, and treated with Amersham ECL Western Blotting Detection Reagents (Cat No. RPN2108). The blot was exposed to a film in a dark room, and the film was developed using an automatic developer. Bands on the SDS-PAGE gel were found to be EPO, and the EPO bands of different sizes resulted from the degree of glycosylation of EPO (see, FIG. 10).

2) Isoelectric Focusing (IEF)

Figure 11:
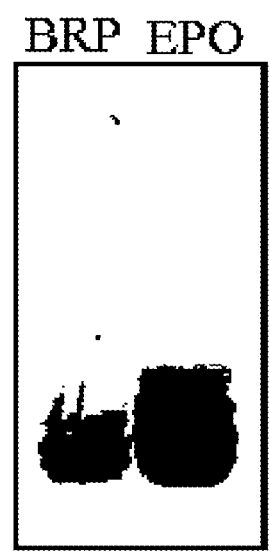
FIG. 11 shows the results of isoelectric focusing of the recombinant EPO purified in Example 4.

The culture supernatant concentrate and the recombinant EPO, purified in Example 4, were mixed with a sample buffer (Invitrogen, Cat No. LC5371) at a 1:1 ratio, and loaded onto an isoelectric focusing gel (Invitrogen, Cat No. EC6655B) along with BRP recombinant hEPO (European Pharmacopoeia Commission Cat No. E1515000) and an IEF standard marker. Isoelectric focusing started at a low voltage and was then carried out at a high voltage. The IEF gel was fixed with a fixing solution containing 12% TCA and 3% sulfosalicylic acid for 30 min with gentle agitation, and stained with Coomassie Brilliant Blue 8250 (Amresco Cat No. 6104-59-2). EPO was observed at isoelectric points thereof (see, FIG. 11).

3) Evaluation of Titer and Activity Using TF-1 Cells

TF-1 cells (ATCC Cat No. CRL-2003) were cultured in RPMI 1640 (Welgene Cat No. LM 011-03) supplemented with 10% FBS, 10 μM β-mercaptoethanol, 20 μg/ml transferrin and 12 ng/ml of GM-CSF, and harvested through centrifugation at 1,000 rpm for 5 min. The TF-1 cells were washed with phosphate buffer twice, and washed once with an assay medium containing 2% FBS, 100 µg/ml of transferrin, 2 mg/ml of protease-free bovine serum and 1% penicillin/streptomycin. 50 µl of the assay medium was added to each well of a 96-well plate. 25 µl of a sample and a standard were added to a first well and serially diluted three times to a final concentration of 1 µg/ml. The TF-1 cells, washed with the assay medium, were added to each well at a density of $2\times10^4/50$ µl/well. After the plate was incubated in a 5% $CO_2$ incubator at 37 r for about 72 hrs, 20 µl of CellTiter One Solution Reagent (Promega Cat No. G4102) was added to each well. The plate was incubated in a 5% $CO_2$ incubator at 37 r for 4 hrs for color development. After the plate was well swirled, absorbance was measured at 490 nm using an ELISA leader (Molecular Dynamics). No marked difference was observed between the activity of recombinant EPO expressed by X0GC/GEPO and that of a standard form.

Example 10

Adaptation of Single-Cell Clones to Serum-Free Medium

X1GC/GEPO9629 (DG44) and X0GC/GEPO9603 (DG44) strains were grown to reach more than 90% confluency in two T-175 flasks containing a selection medium, a-MEM (Welgene, Cat No. LM008-02) supplemented with 10% dialyzed fetal bovine serum), 1% penicillin-streptomycin and 800 µg/ml of Geneticin (Mediatech, Cat No. 61-234 RG). Cells were detached with 0.5% Trypsin (Gibco., Cat No. 15400-054) and centrifuged. The cell pellet was suspended in JRH's EX-CELL CD CHO (Cat No. 14360) medium supplemented with 8 mM glutamine. The cell suspension in the serum-free medium was placed into a T-175 flask and subjected to stationary culture in a $CO_2$ incubator. After 3 days, suspending cells were harvested through centrifugation and transferred into a T-25 flask, followed by stationary culture. After 9 days, suspending cells were collected again and assayed for cell number, growth rate and viability. This procedure was repeated until cell division occurred in about 24 hrs and cell viability reached higher than 80%. In order to determine the expression patterns of X0GC/GEPO9603 (DG44) and X1GC/GEPO9629 (DG44) cells completely assimilated to the non-serum condition, $1.0\times10^5$ cells/ml were inoculated in a 500-ml spinner bottle (Bellco) containing 200 ml of culture medium and cultured with stirring at 50 rpm. After 7 days, 100 ml of the medium was exchanged with fresh medium, and cells were cultured at 33° C. Culture supernatants were collected at 24-hr intervals and assayed for the acidic isomer content of the expressed EPO. X0GC/GEPO9603 (DG44) and X1GC/GEPO9629 (DG44) cells, completely assimilated to a serum-free condition, exhibited isoelectric focusing profiles similar to those of conventional EPO produced in a cell factory.

INDUSTRIAL APPLICABILITY

As described hereinbefore, the present invention provides vectors containing a DHFR promoter from which GC-rich sequences are partially or entirely removed and cell lines transformed with the vectors. The vectors enable the selection of a cell line producing human EPO in a shorter time using a lower concentration of a DHFR inhibitor, thereby shortening the time required to establish a cell line that produces high levels of EPO. Also, the cell lines are capable of mass producing a desired recombinant protein at high yield. Thus, the present invention is capable of more effectively improving a gene amplification system, which is a strategy for producing a desired protein in animal cells.

The invention claimed is:

1. An isolated inducible high-expression cassette comprising the nucleotide sequence of SEQ ID NO. 10, wherein one or more CCGCCC repeat sequences are removed from the GC-rich region of positions 8 to 67 of SEQ ID NO. 10.

2. The inducible high-expression cassette according to claim 1, wherein the GC-rich region contains one or zero CCGCCC repeat sequences.

3. An inducible high-expression cassette comprising any one nucleotide sequence selected from the group consisting of nucleotide sequences of SEQ ID Nos. 7, 8, and 9.

4. An expression vector comprising the inducible high-expression cassette of claim 1.

5. The expression vector according to claim 4, which further comprises a gene encoding a physiologically active polypeptide.

6. The expression vector according to claim 5, wherein the physiologically active polypeptide is human erythropoietin.

7. An expression vector comprising any one nucleotide sequence selected from the group consisting of nucleotide sequences of SEQ ID Nos. 1, 2, and 3.

8. An expression vector comprising the nucleotide sequence of SEQ ID No. 5 or 6.

9. A cell line transformed with the expression vector of claim 8.

10. The cell line according to claim 9, which has accession number KCTC10991BP or KCTC10992BP.

11. A cell line transformed with the expression vector of claim 5.

12. The cell line according to claim 11, which is a CHO cell line.

13. The cell line according to claim 12, wherein the CHO cell line is deficient in a dihydrofolate reductase gene.

14. The cell line according to claim 12, which has accession number KCTC10993BP, KCTC10994BP or KCTC10995BP.

15. A method of producing a recombinant protein comprising the steps of:
  (a) transforming an animal cell line with an expression vector including the isolated inducible high-expression cassette of claim 1 and a gene encoding the recombinant protein;

(b) culturing the transformed animal cell line in presence of a dihydrofolate reductase inhibitor; and
(c) isolating the recombinant protein.

16. The method according to claim 15, wherein the recombinant protein is human erythropoietin.

17. The method according to claim 16, which further comprises purifying erythropoietin having a high sialic acid content.

18. The method according to claim 15, wherein the animal cell line of step (a) is a dihydrofolate reductase-deficient CHO cell line.

19. The method according to claim 15, wherein the transformed animal cell line of step (b) has accession number KCTC10993BP, KCTC10994BP or KCTC10995BP.

20. A method of producing a recombinant protein comprising the steps of:
(a) transforming an animal cell line with an expression vector including the isolated inducible high-expression cassette of claim 3 and a gene encoding the recombinant protein;
(b) culturing the transformed animal cell line in presence of a dihydrofolate reductase inhibitor to produce the recombinant protein; and
(c) isolating the recombinant protein.

* * * * *

SEQUENCE LISTING

```
<160> NUMBER OF SEQ ID NOS: 18

<210> SEQ ID NO 1
<211> LENGTH: 9227
<212> TYPE: DNA
<213> ORGANISM: Artificial Sequence
<220> FEATURE:
<223> OTHER INFORMATION: Synthetic construct of X0GC/GEPO vector

<400> SEQUENCE: 1
gacggatcgg gagatccgac atgataagat acattgatga gtttggacaa accacaacta      60
gaatgcagtg aaaaaaatgc tttatttgtg aaatttgtga tgctattgct ttatttgtaa     120
ccattataag ctgcaataaa caagttaaca acaacaattg cattcatttt atgtttcagg     180
ttcaggggga ggtgtgggag gttttttaaa gcaagtaaaa cctctacaaa tgtggtatgg     240
ctgattatga tctctagtca aggcactata catcaaatat tccttattaa cccctttaca     300
aattaaaaag ctaaaggtac acaattttg agcatagtta ttaatagcag acactctatg      360
cctgtgtgga gtaagaaaaa acagtatgtt atgattataa ctgttatgcc tacttataaa     420
ggttacagaa tattttcca taattttctt gtatagcagt gcagctttt cctttgtggt       480 gtaaatagca aagcaagcaa gagttctatt actaaacaca gcatgactca aaaaacttag     540
caattctgaa ggaaagtcct tggggtcttc tacctttctc ttcttttttg gaggagtaga     600
atgttgagag tcagcagtag cctcatcatc actagatggc atttcttctg agcaaaacag     660
```

```
gttttcctca ttaaaggcat tccaccactg ctcccattca tcagttccat aggttggaat    720
ctaaaataca caaacaatta gaatcagtag tttaacacat tatacactta aaaattttat    780 atttaccttta gagctttaaa tctctgtagg tagtttgtcc aattatgtca caccacagaa    840
gtaaggttcc ttcacaaaga tccaaagcca gcaaaagtcc catggtctta taaaaatgca    900
tagctttagg aggggagcag agaacttgaa agcatcttcc tgttagtctt tcttctcgta    960
gacttcaaac ttatacttga tgccttttc ctcctggacc tcagagagga cgcctgggta    1020
ttctgggaga agtttatatt tccccaaatc aatttctggg aaaaacgtgt cactttcaaa    1080
ttcctgcatg atccttgtca caaagagtct gaggtggcct ggttgattca tggcttcctg    1140
gtaaacagaa ctgcctccga ctatccaaac catgtctact ttacttgcca attccggttg    1200
ttcaataagt cttaaggcat catccaaact tttggcaaga aaatgagctc ctcgtggtgg    1260
ttctttgagt tctctactga aactatatt aattctgtcc tttaaaggtc gattcttctc    1320
aggaatggag aaccaggttt tcctacccat aatcaccaga ttctgtttac cttccactga    1380
agaggttgtg gtcattcttt ggaagtactt gaactcgttc ctgagcggag gccagggtag    1440
gtctccgttc ttgccaatcc ccatattttg ggacacggcg acgatgcagt tcaatggtcg    1500
aaccatgatg gcagcgggga taaaatccta ccagccttca cgctaggatt gccgtcaagt    1560
ttggcgcgaa atcgcagccc tgagctgtgg atctcccgat cccctatggt gcactctcag    1620
tacaatctgc tctgatgccg catagttaag ccagtatctg ctccctgctt gtgtgttgga    1680
ggtcgctgag tagtgcgcga gcaaaattta agctacaaca aggcaaggct tgaccgacaa    1740
ttgcatgaag aatctgctta gggttaggcg ttttgcgctg cttcgcgatg tacgggccag    1800
atatacgcgt tgacattgat tattgactag ttattaatag taatcaatta cggggtcatt    1860
agttcatagc ccatatatgg agttccgcgt tacataactt acggtaaatg gcccgcctgg    1920
ctgaccgccc aacgaccccc gcccattgac gtcaataatg acgtatgttc ccatagtaac    1980
gccaataggg actttccatt gacgtcaatg ggtggagtat ttacggtaaa ctgcccactt    2040
ggcagtacat caagtgtatc atatgccaag tacgccccct attgacgtca atgacggtaa    2100
atggcccgcc tggcattatg cccagtacat gaccttatgg gactttccta cttggcagta    2160
catctacgta ttagtcatcg ctattaccat ggtgatgcgg ttttggcagt acatcaatgg    2220
gcgtggatag cggtttgact cacggggatt tccaagtctc cacccccattg acgtcaatgg    2280 gagtttgttt tggcaccaaa atcaacggga ctttccaaaa tgtcgtaaca actccgcccc    2340
attgacgcaa atgggcggta ggcgtgtacg gtgggaggtc tatataagca gagctctctg    2400
gctaactaga gaacccactg cttactggct tatcgaaatt aatacgactc actatagga    2460 gacccaagct tggtaccgag ctcggatcca ctagtaacgg ccgccagtgt gctggaattc    2520
tgcagattcg aggtcgacgg tatcgataag cttccaagcg cggagatggg ggtgcacggt    2580
gagtactcgc gggctgggcg ctcccgcccg cccgggtccc tgtttgagcg ggatttagc    2640 gccccggcta ttgccagga ggtggctggg ttcaaggacc ggcgacttgt caaggacccc    2700
ggaaggggga gggggtggg gcagcctcca cgtgccagcg gggacttggg ggagtccttg    2760
gggatggcaa aaacctgacc tgtgaagggg acacagtttg ggggttgagg ggaagaaggt    2820
ttgggggttc tgctgtgcca gtggagagga agctgataag ctgataacct gggcgctgga    2880
gccaccactt atctgccaga ggggaagcct ctgtcacacc aggattgaag tttggccgga    2940
gaagtggatg ctggtagctg ggggtggggt gtgcacacgg cagcaggatt gaatgaaggc    3000
cagggaggca gcacctgagt gcttgcatgg ttggggacag gaaggacgag ctggggcaga    3060
```

```
gacgtgggga tgaaggaagc tgtccttcca cagccaccct tctccctccc cgcctgactc      3120
tcagcctggc tatctgttct agaatgtcct gcctggctgt ggcttctcct gtccctgctg      3180
tcgctccctc tgggcctccc agtcctgggc ccccaccac gcctcatctg tgacagccga       3240
gtcctggaga ggtacctctt ggaggccaag gaggccgaga atatcacggt gaggaccctt      3300
ccccagcaca ttccacagaa ctcacgctca gggcttcagg gaactcctcc cagatccagg      3360
aacctggcac ttggtttagg gtggagttgg gaagctagac actgccccccc tacataagaa     3420 taagtctggt ggccccaaac catacctgga aactaggcaa ggagcaaagc cagcagatcc      3480
tacggcctgt gggccagggc cagagccttc agggacccctt gactccccgg gctgtgtgca     3540
tttcagacgg gctgtgctga acactgcagc ttgaatgaga atatcactgt cccagacacc      3600
aaagttaatt tctatgcctg gaagaggatg gaggtgagtt cctttttttt tttttttcct      3660
ttcttttgga gaatctcatt tgcgagcctg attttggatg aaagggagaa tgatcgaggg      3720
aaaggtaaaa tggagcagca gagatgaggc tgcctgggcg cagaggctca cgtctataat      3780
cccaggctga gatggccgag atgggagaat tgcttgagcc ctggagtttc agaccaacct      3840
aggcagcata gtgagatccc ccatctctac aaacatttaa aaaaattagt caggtgaagt      3900
ggtgcatggt ggtagtccca gatatttgga aggctgaggc gggaggatcg cttgagccca      3960
ggaatttgag gctgcagtga gctgtgatca ccactgca ctccagcctc agtgacagag        4020
tgaggccctg tctcaaaaaa gaaagaaaa aagaaaaata atgagggctg tatggaatac       4080
attcattatt cattcactca ctcactcact cattcattca ttcattcatt caacaagtct      4140
tattgcatac cttctgtttg ctcagcttgg tgcttgggc tgctgagggg caggagggag       4200
agggtgacat gggtcagctg actcccagag tccactccct gtaggtcggg cagcaggccg      4260
tagaagtctg gcagggcctg gccctgctgt cggaagctgt cctgcggggc caggccctgt      4320
tggtcaactc ttcccagccg tgggagcccc tgcagctgca tgtggataaa gccgtcagtg      4380
gccttcgcag cctcaccact ctgcttcggg ctctgggagc ccaggtgagt aggagcggac      4440
acttctgctt gcccttttctg taagaagggg agaagggtct tgctaaggag tacaggaact    4500
gtccgtattc cttcccttc tgtggcactg cagcgacctc ctgttttctc cttggcagaa      4560
ggaagccatc tcccctccag atgcggcctc agctgctcca ctccgaacaa tcactgctga     4620
cactttccgc aaactcttcc gagtctactc caatttcctc cggggaaagc tgaagctgta     4680
cacaggggag gcctgcagga caggggacag atgaccagct tgatatcgaa ttatccatca    4740
cactggcggc cgctcgagca tgcatctaga gggcccatt ctatagtgtc acctaaatgc     4800
tagagctcgc tgatcagcct cgactgtgcc ttctagttgc cagccatctg ttgtttgccc    4860
ctcccccgtg ccttccttga ccctggaagg tgccactccc actgtccttt cctaataaaa    4920
tgaggaaatt gcatcgcatt gtctgagtag gtgtcattct attctggggg gtggggtggg   4980
gcaggacagc aagggggagg attgggaaga caatagcagg catgctgggg atgcggtggg   5040
ctctatggct tctgaggcgg aaagaaccag ctggggctct aggggggtatc cccacgcgcc   5100 ctgtagcggc gcattaagcg cggcgggtgt ggtggttacg cgcagcgtga ccgctacact   5160
tgccagcgcc ctagcgcccg ctcctttcgc tttcttccct tcctttctcg ccacgttcgc   5220
cggctttccc cgtcaagctc taaatcgggg gctcccttta gggttccgat ttagtgcttt   5280
acggcacctc gaccccaaaa aacttgatta gggtgatggt tcacgtagtg gccatcgcc    5340 ctgatagacg gttttttcgcc ctttgacgtt ggagtccacg ttctttaata gtggactctt   5400
```

```
gttccaaact ggaacaacac tcaaccctat ctcggtctat tcttttgatt tataagggat   5460
tttgccgatt tcggcctatt ggttaaaaaa tgagctgatt taacaaaaat ttaacgcgaa   5520
ttaattctgt ggaatgtgtg tcagttaggg tgtggaaagt ccccaggctc cccagcaggc   5580
agaagtatgc aaagcatgca tctcaattag tcagcaacca ggtgtggaaa gtccccaggc   5640
tccccagcag gcagaagtat gcaaagcatg catctcaatt agtcagcaac catagtcccg   5700
cccctaactc cgcccatccc gcccctaact ccgcccagtt ccgcccattc tccgcccat    5760
ggctgactaa ttttttttat ttatgcagag gccgaggccg cctctgcctc tgagctattc   5820
cagaagtagt gaggaggctt ttttggaggc ctaggctttt gcaaaaagct cccgggagct   5880
tgtatatcca ttttcggatc tgatcaagag acaggatgag gatcgtttcg catgattgaa   5940
caagatggat tgcacgcagg ttctccggcc gcttgggtgg agaggctatt cggctatgac   6000
tgggcacaac agacaatcgg ctgctctgat gccgccgtgt tccggctgtc agcgcagggg   6060
cgcccggttc ttttgtcaa gaccgacctg tccggtgccc tgaatgaact gcaggacgag    6120
gcagcgcggc tatcgtggct ggccacgacg ggcgttcctt gcgcagctgt gctcgacgtt   6180
gtcactgaag cgggaaggga ctggctgcta ttgggcgaag tgccggggca ggatctcctg   6240
tcatctcacc ttgctcctgc cgagaaagta tccatcatgg ctgatgcaat gcggcggctg   6300
catacgcttg atccggctac ctgcccattc gaccaccaag cgaaacatcg catcgagcga   6360
gcacgtactc ggatggaagc cggtcttgtc gatcaggatg atctggacga agagcatcag   6420
gggctcgcgc cagccgaact gttcgccagg ctcaaggcgc gcatgcccga cggcgaggat   6480
ctcgtcgtga cccatggcga tgcctgcttg ccgaatatca tggtggaaaa tggccgcttt   6540
tctggattca tcgactgtgg ccggctgggt gtggcggacc gctatcagga catagcgttg   6600
gctacccgtg atattgctga agagcttggc ggcgaatggg ctgaccgctt cctcgtgctt   6660
tacggtatcg ccgctcccga ttcgcagcgc atcgccttct atcgccttct tgacgagttc   6720
ttctgagcgg gactctgggg ttcgaaatga ccgaccaagc gacgcccaac ctgccatcac   6780
gagatttcga ttccaccgcc gccttctatg aaaggttggg cttcggaatc gttttccggg   6840
acgccggctg gatgatcctc cagcgcgggg atctcatgct ggagttcttc gcccaccccca  6900
acttgtttat tgcagcttat aatggttaca ataaagcaa tagcatcaca aatttcacaa    6960
ataaagcatt ttttttcactg cattctagtt gtggtttgtc caaactcatc aatgtatctt  7020
atcatgtctg tataccgtcg acctctagct agagcttggc gtaatcatgg tcatagctgt   7080
ttcctgtgtg aaattgttat ccgctcacaa ttccacacaa catacgagcc ggaagcataa   7140
agtgtaaagc ctggggtgcc taatgagtga gctaactcac attaattgcg ttgcgctcac   7200
tgcccgcttt ccagtcggga aacctgtcgt gccagctgca ttaatgaatc ggccaacgcg   7260
cggggagagg cggtttgcgt attgggcgct cttccgcttc ctcgctcact gactcgctgc   7320
gctcggtcgt tcggctgcgg cgagcggtat cagctcactc aaaggcggta atacggttat   7380
ccacagaatc agggggataac gcaggaaaga acatgtgagc aaaaggccag caaaaggcca   7440
ggaaccgtaa aaaggccgcg ttgctggcgt ttttccatag gctccgcccc cctgacgagc   7500
atcacaaaaa tcgacgctca agtcagaggt ggcgaaaccc gacaggacta taaagatacc   7560
aggcgtttcc ccctggaagc tccctcgtgc gctctcctgt tccgaccctg ccgcttaccg   7620
gatacctgtc cgcctttctc ccttcgggaa gcgtggcgct ttctcatagc tcacgctgta   7680
ggtatctcag ttcggtgtag gtcgttcgct ccaagctggg ctgtgtgcac gaaccccccg   7740
ttcagcccga ccgctgcgcc ttatccggta actatcgtct tgagtccaac ccggtaagac   7800
```

```
acgacttatc gccactggca gcagccactg gtaacaggat tagcagagcg aggtatgtag    7860
gcggtgctac agagttcttg aagtggtggc ctaactacgg ctacactaga agaacagtat    7920
ttggtatctg cgctctgctg aagccagtta ccttcggaaa aagagttggt agctcttgat    7980
ccggcaaaca aaccaccgct ggtagcggtg gttttttttgt ttgcaagcag cagattacgc    8040
gcagaaaaaa aggatctcaa gaagatcctt tgatcttttc tacggggtct gacgctcagt    8100
ggaacgaaaa ctcacgttaa gggattttgg tcatgagatt atcaaaaagg atcttcacct    8160
agatccttt aaattaaaaa tgaagtttta aatcaatcta agtatatat gagtaaactt    8220
ggtctgacag ttaccaatgc ttaatcagtg aggcacctat ctcagcgatc tgtctatttc    8280
gttcatccat agttgcctga ctccccgtcg tgtagataac tacgatacgg gagggcttac    8340
catctggccc cagtgctgca atgataccgc gagacccacg ctcaccggct ccagatttat    8400
cagcaataaa ccagccagcc ggaagggccg agcgcagaag tggtcctgca actttatccg    8460
cctccatcca gtctattaat tgttgccggg aagctagagt aagtagttcg ccagttaata    8520
gtttgcgcaa cgttgttgcc attgctacag gcatcgtggt gtcacgctcg tcgtttggta    8580
tggcttcatt cagctccggt tcccaacgat caaggcgagt tacatgatcc cccatgttgt    8640
gcaaaaaagc ggttagctcc ttcggtcctc cgatcgttgt cagaagtaag ttggccgcag    8700
tgttatcact catggttatg gcagcactgc ataattctct tactgtcatg ccatccgtaa    8760
gatgcttttc tgtgactggt gagtactcaa ccaagtcatt ctgagaatag tgtatgcggc    8820
gaccgagttg ctcttgcccg gcgtcaatac gggataatac cgcgccacat agcagaactt    8880
taaaagtgct catcattgga aaacgttctt cggggcgaaa actctcaagg atcttaccgc    8940
tgttgagatc cagttcgatg taacccactc gtgcacccaa ctgatcttca gcatctttta    9000
ctttcaccag cgtttctggg tgagcaaaaa caggaaggca aaatgccgca aaaaagggaa    9060
taagggcgac acggaaatgt tgaatactca tactcttcct ttttcaatat tattgaagca    9120
tttatcaggg ttattgtctc atgagcggat acatatttga atgtatttag aaaaataaac    9180
aaataggggt tccgcgcaca tttccccgaa aagtgccacc tgacgtc              9227
```

<210> SEQ ID NO 2  
<211> LENGTH: 8635  
<212> TYPE: DNA  
<213> ORGANISM: Artificial Sequence  
<220> FEATURE:  
<223> OTHER INFORMATION: Synthetic construct of X1GC/GEPO vector

<400> SEQUENCE: 2

```
gacggatcgg gagatccatt ctccgcccca tggctgacta attttttta tttatgcaga     60
ggccgaggcc gcctctgcct ctgagctatt ccagaagtag tgaggaggct ttttggagg    120
cctaggcttt tgcaaaaagc tcccgggatg gttcgaccat tgaactgcat cgtcgccgtg    180
tcccaaaata tggggattgg caagaacgga aacctaccct ggcctccgct caggaacgag    240
ttcaagtact ccaaagaat gaccacaacc tcttcagtgg aaggtaaaca gaatctggtg    300
attatgggta ggaaaacctg gttctccatt cctgagaaga atcgaccttt aaaggacaga    360
attaatatag ttctcagtag agaactcaaa gaaccaccac gaggagctca ttttcttgcc    420
aaaagtttgg atgatgcctt aagacttatt gaacaaccgg aattggcaag taaagtagac    480
atggtttgga tagtcggagg cagttctgtt taccaggaag ccatgaatca accaggccac    540
ctcagactct ttgtgacaag gatcatgcag gaatttgaaa gtgacacgtt tttcccagaa    600
```

```
attgatttgg ggaaatataa acttctccca gaatacccag gcgtcctctc tgaggtccag    660
gaggaaaaag gcatcaagta taagtttgaa gtctacgaga agaaagacta acaggttcga    720
aatgaccgac caagcgacgc ccaacctgcc atcacgagat ttcgattcca ccgccgcctt    780
ctatgaaagg ttgggcttcg gaatcgtttt ccgggacgcc ggctggatga tcctccagcg    840
cggggatctc atgctggagt tcttcgccca ccccaacttg tttattgcag cttataatgg    900
ttacaaataa agcaatagca tcacaaattt cacaaataaa gcattttttt cactgcattc    960
tagttgtggt ttgtccaaac tcatcaatgt atcttatcat gtctgggatc tcccgatccc   1020
ctatggtgca ctctcagtac aatctgctct gatgccgcat agttaagcca gtatctgctc   1080
cctgcttgtg tgttggaggt cgctgagtag tgcgcgagca aaatttaagc tacaacaagg   1140
caaggcttga ccgacaattg catgaagaat ctgcttaggg ttaggcgttt tgcgctgctt   1200
cgcgatgtac gggccagata tacgcgttga cattgattat tgactagtta ttaatagtaa   1260
tcaattacgg ggtcattagt tcatagccca tatgtggagt tccgcgttac ataacttacg   1320
gtaaatggcc cgcctggctg accgcccaac gacccccgcc cattgacgtc aataatgacg   1380
tatgttccca tagtaacgcc aatagggact ttccattgac gtcaatgggt ggagtattta   1440
cggtaaactg cccacttggc agtacatcaa gtgtatcata tgccaagtac gccccctatt   1500
gacgtcaatg acggtaaatg gcccgcctgg cattatgccc agtacatgac cttatgggac   1560
tttcctactt ggcagtacat ctacgtatta gtcatcgcta ttaccatggt gatgcggttt   1620
tggcagtaca tcaatgggcg tggatagcgg tttgactcac ggggatttcc aagtctccac   1680
cccattgacg tcaatgggag tttgttttgg caccaaaatc aacgggactt tccaaaatgt   1740
cgtaacaact ccgccccatt gacgcaaatg ggcggtaggc gtgtacggtg gaggtctat   1800 ataagcagag ctctctggct aactagagaa cccactgctt actggcttat cgaaattaat   1860
acgactcact atagggagac ccaagctggc tagcgtttaa acttaagctt ggtaccgagc   1920
tcggatccac tagtaacggc cgccagtgtg ctggaattct gcagattcga ggtcgacggt   1980
atcgataagc ttccaagcgc ggagatgggg gtgcacggtg agtactcgcg ggctgggcgc   2040
tcccgcccgc ccgggtccct gtttgagcgg ggatttagcg ccccggctat ggccaggag   2100 gtggctgggt tcaaggaccg gcgacttgtc aaggaccccg gaaggggag ggggtgggg    2160 cagcctccac gtgccagcgg ggacttgggg gagtccttgg ggatggcaaa aacctgacct   2220
gtgaagggga cacagtttgg gggttgaggg gaagaaggtt tgggggttct gctgtgccag   2280
tggagaggaa gctgataagc tgataacctg ggcgctggag ccaccactta tctgccagag   2340
gggaagcctc tgtcacacca ggattgaagt ttggccggag aagtggatgc tggtagctgg   2400
gggtggggtg tgcacacggc agcaggattg aatgaaggcc agggaggcag cacctgagtg   2460
cttgcatggt tggggacagg aaggacgagc tggggcagag acgtggggat gaaggaagct   2520
gtccttccac agccacccct ctccctcccc gcctgactct cagcctggct atctgttcta   2580
gaatgtcctg cctggctgtg gcttctcctg tccctgctgt cgctccctct gggcctccca   2640
gtcctgggcg ccccaccacg cctcatctgt gacagccgag tcctggagag gtacctcttg   2700
gaggccaagg aggccgagaa tatcacggtg agacccttc cccagcacat tccacagaac   2760
tcacgctcag gcttcaggg aactcctccc agatccagga acctggcact tggtttaggg   2820
tggagttggg aagctagaca ctgccccct acataagaat aagtctggtg gccccaaacc   2880 ataccctggaa actaggcaag gagcaaagcc agcagatcct acggcctgtg gccagggcc   2940 agagccttca gggacccttg actcccggg ctgtgtgcat ttcagacggg ctgtgctgaa   3000
```

```
cactgcagct tgaatgagaa tatcactgtc ccagacacca agttaatttc tatgcctgg      3060 aagaggatgg aggtgagttc cttttttttt tttttccctt tcttttggag aatctcattt      3120
gcgagcctga ttttggatga aagggagaat gatcgaggga aaggtaaaat ggagcagcag      3180
agatgaggct gcctgggcgc agaggctcac gtctataatc ccaggctgag atggccgaga      3240
tgggagaatt gcttgagccc tggagtttca gaccaaccta ggcagcatag tgagatcccc      3300
catctctaca aacatttaaa aaaattagtc aggtgaagtg gtgcatggtg gtagtcccag      3360
atatttggaa ggctgaggcg ggaggatcgc ttgagcccag gaatttgagg ctgcagtgag      3420
ctgtgatcac accactgcac tccagcctca gtgacagagt gaggccctgt ctcaaaaaag      3480 aaagaaaaa agaaaaataa tgagggctgt atggaataca ttcattattc attcactcac      3540
tcactcactc attcattcat tcattcattc aacaagtctt attgcatacc ttctgtttgc      3600
tcagcttggt gcttggggct gctgagggc aggagggaga gggtgacatg ggtcagctga      3660
ctcccagagt ccactccctg taggtcgggc agcaggccgt agaagtctgg cagggcctgg      3720
ccctgctgtc ggaagctgtc ctgcggggcc aggccctgtt ggtcaactct cccagccgt      3780 gggagcccct gcagctgcat gtggataaag ccgtcagtgg ccttcgcagc ctcaccactc      3840
tgcttcgggc tctgggagcc caggtgagta ggagcggaca cttctgcttg ccctttctgt      3900
aagaagggga aagggtcttt gctaaggagt acaggaactg tccgtattcc ttccctttct      3960
gtggcactgc agcgacctcc tgttttctcc ttggcagaag gaagccatct cccctccaga      4020
tgcggcctca gctgctccac tccgaacaat cactgctgac actttccgca aactcttccg      4080
agtctactcc aatttcctcc ggggaaagct gaagctgtac acaggggagg cctgcaggac      4140
aggggacaga tgaccagctt gatatcgaat tatccatcac actggcggcc gctcgagtct      4200
agagggcccg tttaaacccg ctgatcagcc tcgactgtgc cttctagttg ccagccatct      4260
gttgtttgcc cctcccccgt gccttccttg accctggaag gtgccactcc cactgtcctt      4320
tcctaataaa atgaggaaat tgcatcgcat tgtctgagta ggtgtcattc tattctgggg      4380
ggtggggtgg ggcaggacag caaggggga gattgggaag acaatagcag gcatgctggg      4440
gatgcggtgg gctctatggc ttctgaggcg gaaagaacca gctggggctc tagggggtat      4500
ccccacgcgc cctgtagcgg cgcattaagc gcggcgggtg tggtggttac gcgcagcgtg      4560
accgctacac ttgccagcgc cctagcgccc gctccttttcg ctttcttccc ttcctttctc      4620
gccacgttcg ccggctttcc ccgtcaagct ctaaatcggg ggctcccttt agggttccga      4680
tttagtgctt tacggcacct cgaccccaaa aaacttgatt agggtgatgg ttcacgtagt      4740
gggccatcgc cctgatagac ggtttttcgc cctttgacgt tggagtccac gttctttaat      4800
agtggactct tgttccaaac tggaacaaca ctcaaccta tctcggtcta ttcttttgat      4860
ttataaggga ttttgccgat ttcggcctat tggttaaaaa atgagctgat ttaacaaaaa      4920
tttaacgcga attaattctg tggaatgtgt gtcagttagg gtgtggaaag tccccaggct      4980
ccccagcagg cagaagtatg caaagcatgc atctcaatta gtcagcaacc aggtgtggaa      5040 agtcccagg ctcccagca ggcagaagta tgcaaagcat gcatctcaat tagtcagcaa      5100
ccatagtccc gcccctaact ccgcccatcc cgcccctaac tccgcccagt tccgcccatt      5160
ctccgcccca tggctgacta attttttttta tttatgcaga ggccgaggcc gcctctgcct      5220
ctgagctatt ccagaagtag tgaggaggct ttttggagg cctaggcttt tgcaaaaagc      5280
tcccgggagc ttgtatatcc attttcggat ctgatcaaga gacaggatga ggatcgtttc      5340
```

```
gcatgattga acaagatgga ttgcacgcag gttctccggc cgcttgggtg gagaggctat      5400
tcggctatga ctgggcacaa cagacaatcg gctgctctga tgccgccgtg ttccggctgt      5460
cagcgcaggg gcgcccggtt cttttgtca agaccgacct gtccggtgcc ctgaatgaac       5520
tgcaggacga ggcagcgcgg ctatcgtggc tggccacgac gggcgttcct tgcgcagctg      5580
tgctcgacgt tgtcactgaa gcgggaaggg actggctgct attgggcgaa gtgccggggc      5640
aggatctcct gtcatctcac cttgctcctg ccgagaaagt atccatcatg gctgatgcaa      5700
tgcggcggct gcatacgctt gatccggcta cctgcccatt cgaccaccaa gcgaaacatc      5760
gcatcgagcg agcacgtact cggatggaag ccggtcttgt cgatcaggat gatctggacg      5820
aagagcatca ggggctcgcg ccagccgaac tgttcgccag gctcaaggcg cgcatgcccg      5880
acggcgagga tctcgtcgtg acccatggcg atgcctgctt gccgaatatc atggtggaaa      5940
atggccgctt ttctggattc atcgactgtg gccggctggg tgtggcggac cgctatcagg      6000
acatagcgtt ggctacccgt gatattgctg aagagcttgg cggcgaatgg gctgaccgct      6060
tcctcgtgct ttacggtatc gccgctcccg attcgcagcg catcgccttc tatcgccttc      6120
ttgacgagtt cttctgagcg ggactctggg gttcgaaatg accgaccaag cgacgcccaa      6180
cctgccatca cgagatttcg attccaccgc cgccttctat gaaaggttgg gcttcggaat      6240
cgttttccgg gacgccggct ggatgatcct ccagcgcggg gatctcatgc tggagttctt      6300
cgcccacccc aacttgttta ttgcagctta taatggttac aaataaagca atagcatcac      6360
aaatttcaca ataaagcat tttttcact gcattctagt tgtggtttgt ccaaactcat       6420
caatgtatct tatcatgtct gtataccgtc gacctctagc tagagcttgg cgtaatcatg      6480
gtcatagctg tttcctgtgt gaaattgtta tccgctcaca attccacaca atacgagc        6540 cggaagcata agtgtaaag cctggggtgc ctaatgagtg agctaactca cattaattgc       6600
gttgcgctca ctgcccgctt tccagtcggg aaacctgtcg tgccagctgc attaatgaat      6660
cggccaacgc gcggggagag gcggtttgcg tattgggcgc tcttccgctt cctcgctcac      6720
tgactcgctg cgctcggtcg ttcggctgcg gcgagcggta tcagctcact caaaggcggt      6780
aatacggtta tccacagaat caggggataa cgcaggaaag aacatgtgag caaaaggcca      6840
gcaaaaggcc aggaaccgta aaaaggccgc gttgctggcg ttttccata ggctccgccc       6900 ccctgacgag catcacaaaa atcgacgctc aagtcagagg tggcgaaacc cgacaggact      6960
ataaagatac caggcgtttc ccctggaag ctccctcgtg cgctctcctg ttccgaccct       7020
gccgcttacc ggatacctgt ccgcctttct cccttcggga agcgtggcgc tttctcatag      7080
ctcacgctgt aggtatctca gttcggtgta ggtcgttcgc tccaagctgg gctgtgtgca      7140 cgaaccccc gttcagcccg accgctgcgc cttatccggt aactatcgtc ttgagtccaa       7200
cccggtaaga cacgacttat cgccactggc agcagccact ggtaacagga ttagcagagc      7260
gaggtatgta ggcggtgcta cagagttctt gaagtggtgg cctaactacg gctacactag      7320
aagaacagta tttggtatct gcgctctgct gaagccagtt accttcggaa aaagagttgg      7380
tagctcttga tccggcaaac aaaccaccgc tggtagcggt ttttttgttt gcaagcagca      7440
gattacgcgc agaaaaaaag gatctcaaga agatcctttg atcttttcta cggggtctga     7500
cgctcagtgg aacgaaaact cacgttaagg gattttggtc atgagattat caaaaaggat      7560
cttcacctag atccttttaa attaaaaatg aagttttaaa tcaatctaaa gtatatatga      7620
gtaaacttgg tctgacagtt accaatgctt aatcagtgag gcacctatct cagcgatctg      7680
tctatttcgt tcatccatag ttgcctgact ccccgtcgtg tagataacta cgatacggga      7740
```

```
gggcttacca tctggcccca gtgctgcaat gataccgcga gacccacgct caccggctcc    7800
agatttatca gcaataaacc agccagccgg aagggccgag cgcagaagtg gtcctgcaac    7860
tttatccgcc tccatccagt ctattaattg ttgccgggaa gctagagtaa gtagttcgcc    7920
agttaatagt ttgcgcaacg ttgttgccat tgctacaggc atcgtggtgt cacgctcgtc    7980
gtttggtatg gcttcattca gctccggttc ccaacgatca aggcgagtta catgatcccc    8040
catgttgtgc aaaaaagcgg ttagctcctt cggtcctccg atcgttgtca gaagtaagtt    8100
ggccgcagtg ttatcactca tggttatggc agcactgcat aattctctta ctgtcatgcc    8160
atccgtaaga tgcttttctg tgactggtga gtactcaacc aagtcattct gagaatagtg    8220
tatgcggcga ccgagttgct cttgcccggc gtcaatacgg gataataccg cgccacatag    8280
cagaacttta aaagtgctca tcattggaaa acgttcttcg gggcgaaaac tctcaaggat    8340
cttaccgctg ttgagatcca gttcgatgta acccactcgt gcacccaact gatcttcagc    8400
atcttttact ttcaccagcg tttctgggtg agcaaaaaca ggaaggcaaa atgccgcaaa    8460
aaagggaata agggcgacac ggaaatgttg aatactcata ctcttccttt ttcaatatta    8520
ttgaagcatt tatcagggtt attgtctcat gagcggatac atatttgaat gtatttagaa    8580
aaataaacaa atagggttc cgcgcacatt tccccgaaaa gtgccacctg acgtc           8635
```

<210> SEQ ID NO 3
<211> LENGTH: 8657
<212> TYPE: DNA
<213> ORGANISM: Artificial Sequence
<220> FEATURE:
<223> OTHER INFORMATION: Synthetic construct of X3GC/GEPO vector

<400> SEQUENCE: 3

```
gacggatcgg gagatcccta actccgccca gttccgccca ttctccgccc catggctgac      60
taattttttt tatttatgca gaggccgagg ccgcctctgc ctctgagcta ttccagaagt     120
agtgaggagg ctttttttgga ggcctaggct tttgcaaaaa gctcccggga tggttcgacc    180
attgaactgc atcgtcgccg tgtcccaaaa tatggggatt ggcaagaacg gaaacctacc    240
ctggcctccg ctcaggaacg agttcaagta cttccaaaga atgaccacaa cctcttcagt    300
ggaaggtaaa cagaatctgg tgattatggg taggaaaacc tggttctcca ttcctgagaa    360
gaatcgacct ttaaaggaca gaattaatat agttctcagt agagaactca agaaccacc     420 acgaggagct cattttcttg ccaaaagttt ggatgatgcc ttaagactta ttgaacaacc    480
ggaattggca agtaaagtag acatggtttg gatagtcgga ggcagttctg tttaccagga    540
agccatgaat caaccaggcc acctcagact ctttgtgaca aggatcatgc aggaatttga    600
aagtgacacg ttttttcccag aaattgattt ggggaaatat aaacttctcc cagaataccc    660
aggcgtcctc tctgaggtcc aggaggaaaa aggcatcaag tataagtttg aagtctacga    720
gaagaaagac taacaggttc gaaatgaccg accaagcgac gcccaacctg ccatcacgag    780
atttcgattc caccgccgcc ttctatgaaa ggttgggctt cggaatcgtt ttccgggacg    840
ccggctggat gatcctccag cgcgggatc tcatgctgga gttcttcgcc caccccaact    900
tgtttattgc agcttataat ggttacaaat aaagcaatag catcacaaat ttcacaaata    960
aagcattttt ttcactgcat tctagttgtg gtttgtccaa actcatcaat gtatcttatc   1020
atgtctggga tctcccgatc cctatggtg cactctcagt acaatctgct ctgatgccgc   1080
atagttaagc cagtatctgc tccctgcttg tgtgttggag gtcgctgagt agtgcgcgag   1140
```

```
caaaatttaa gctacaacaa ggcaaggctt gaccgacaat tgcatgaaga atctgcttag    1200
ggttaggcgt tttgcgctgc ttcgcgatgt acgggccaga tatacgcgtt gacattgatt    1260
attgactagt tattaatagt aatcaattac ggggtcatta gttcatagcc catatatgga    1320
gttccgcgtt acataactta cggtaaatgg cccgcctggc tgaccgccca acgacccccg    1380
cccattgacg tcaataatga cgtatgttcc catagtaacg ccaataggga ctttccattg    1440
acgtcaatgg gtggagtatt tacggtaaac tgcccacttg gcagtacatc aagtgtatca    1500
tatgccaagt acgcccccta ttgacgtcaa tgacggtaaa tggcccgcct ggcattatgc    1560
ccagtacatg accttatggg actttcctac ttggcagtac atctacgtat tagtcatcgc    1620
tattaccatg gtgatgcggt tttggcagta catcaatggg cgtggatagc ggtttgactc    1680
acggggattt ccaagtctcc accccattga cgtcaatggg agtttgtttt ggcaccaaaa    1740
tcaacgggac tttccaaaat gtcgtaacaa ctccgcccca ttgacgcaaa tgggcggtag    1800
gcgtgtacgg tgggaggtct atataagcag agctctctgg ctaactagag aacccactgc    1860
ttactggctt atcgaaatta atacgactca ctatagggag acccaagctg gctagcgttt    1920
aaacttaagc ttggtaccga gctcggatcc actagtaacg gccgccagtg tgctggaatt    1980
ctgcagattc gaggtcgacg gtatcgataa gcttccaggc gcggagatgg gggtgcacgg    2040
tgagtactcg cgggctgggc gctcccgccc gcccgggtcc ctgtttgagc ggggatttag    2100
cgccccggct attggccagg aggtggctgg gttcaaggac cggcgacttg tcaaggaccc    2160
cggaaggggg aggggggtgg ggcagcctcc acgtgccagc ggggacttgg gggagtcctt    2220
ggggatggca aaaacctgac ctgtgaaggg gacacagttt gggggttgag gggaagaagg    2280
tttgggggtt ctgctgtgcc agtggagagg aagctgataa gctgataacc tgggcgctgg    2340
agccaccact tatctgccag aggggaagcc tctgtcacac caggattgaa gtttggccgg    2400
agaagtggat gctggtagct gggggtgggg tgtgcacacg gcagcaggat tgaatgaagg    2460
ccagggaggc agcacctgag tgcttgcatg gttggggaca ggaaggacga gctggggcag    2520
agacgtgggg atgaaggaag ctgtccttcc acagccaccc ttctccctcc ccgcctgact    2580
ctcagcctgg ctatctgttc tagaatgtcc tgcctggctg tggcttctcc tgtccctgct    2640
gtcgctccct ctgggcctcc cagtcctggg cgccccacca cgcctcatct gtgacagccg    2700
agtcctggag aggtacctct tggaggccaa ggaggccgag aatatcacgg tgagacccct    2760
tccccagcac attccacaga actcacgctc agggcttcag ggaactcctc ccagatccag    2820
gaacctggca cttggtttag ggtggagttg ggaagctaga cactgccccc ctacataaga    2880
ataagtctgg tggccccaaa ccatacctgg aaactaggca aggagcaaag ccagcagatc    2940
ctacggcctg tgggccaggg ccagagcctt caggggaccct tgactccccg ggctgtgtgc    3000
atttcagacg ggctgtgctg aacactgcag cttgaatgag aatatcactg tcccagacac    3060
caaagttaat ttctatgcct ggaagaggat ggaggtgagt tccttttttt ttttttttcc    3120
tttcttttgg agaatctcat ttgcgagcct gattttggat gaaagggaga atgatcgagg    3180
gaaaggtaaa atggagcagc agagatgagg ctgcctgggc gcagaggctc acgtctataa    3240
tcccagcctg agatggccga gatgggagaa ttgcttgagc cctggagttt cagaccaacc    3300
taggcagcat agtgagatcc cccatctcta caaacattta aaaaaattag tcaggtgaag    3360
tggtgcatgg tggtagtccc agatatttgg aaggctgagg cgggaggatc gcttgagccc    3420
aggaatttga ggctgcagtg agctgtgatc acaccactgc actccagcct cagtgacaga    3480
gtgaggccct gtctcaaaaa agaaaagaaa aagaaaaat aatgagggct gtatggaata    3540
```

```
cattcattat tcattcactc actcactcac tcattcattc attcattcat tcaacaagtc    3600
ttattgcata ccttctgttt gctcagcttg gtgcttgggg ctgctgaggg gcaggaggga    3660
gagggtgaca tgggtcagct gactcccaga gtccactccc tgtaggtcgg gcagcaggcc    3720
gtagaagtct ggcagggcct ggccctgctg tcggaagctg tcctgcgggg ccaggccctg    3780
ttggtcaact cttcccagcc gtgggagccc ctgcagctgc atgtggataa agccgtcagt    3840
ggccttcgca gcctcaccac tctgcttcgg gctctgggag cccaggtgag taggagcgga    3900
cacttctgct tgccctttct gtaagaaggg gagaagggtc ttgctaagga gtacaggaac    3960
tgtccgtatt ccttcccttt ctgtggcact gcagcgacct cctgttttct ccttggcaga    4020
aggaagccat ctcccctcca gatgcggcct cagctgctcc actccgaaca atcactgctg    4080
acactttccg caaactcttc cgagtctact ccaatttcct ccggggaaag ctgaagctgt    4140
acacagggga ggcctgcagg acaggggaca gatgaccagc ttgatatcga attatccatc    4200
acactggcgg ccgctcgagt ctagagggcc cgtttaaacc cgctgatcag cctcgactgt    4260
gccttctagt tgccagccat ctgttgtttg cccctccccc gtgccttcct tgaccctgga    4320
aggtgccact cccactgtcc tttcctaata aaatgaggaa attgcatcgc attgtctgag    4380
taggtgtcat tctattctgg ggggtggggt ggggcaggac agcaaggggg aggattggga    4440
agacaatagc aggcatgctg gggatgcggt gggctctatg gcttctgagg cggaaagaac    4500
cagctggggc tctaggggt atccccacgc gccctgtagc ggcgcattaa gcgcggcggg    4560
tgtggtggtt acgcgcagcg tgaccgctac acttgccagc gccctagcgc ccgctccttt    4620
cgctttcttc ccttcctttc tcgccacgtt cgccggcttt ccccgtcaag ctctaaatcg    4680
ggggctccct ttagggttcc gatttagtgc tttacggcac ctcgacccca aaaaacttga    4740
ttagggtgat ggttcacgta gtgggccatc gccctgatag acggtttttc gccctttgac    4800
gttggagtcc acgttcttta atagtggact cttgttccaa actggaacaa cactcaaccc    4860
tatctcggtc tattcttttg atttataagg gattttgccg atttcggcct attggttaaa    4920
aaatgagctg atttaacaaa aatttaacgc gaattaattc tgtggaatgt gtgtcagtta    4980
gggtgtggaa agtccccagg ctccccagca ggcagaagta tgcaaagcat gcatctcaat    5040
tagtcagcaa ccaggtgtgg aaagtcccca ggctccccag caggcagaag tatgcaaagc    5100
atgcatctca attagtcagc aaccatagtc ccgcccctaa ctccgcccat cccgccccta    5160
actccgccca gttccgccca ttctccgccc catggctgac taattttttt tatttatgca    5220
gaggccgagg ccgcctctgc ctctgagcta ttccagaagt agtgaggagg cttttttgga    5280
ggcctaggct tttgcaaaaa gctcccggga gcttgtatat ccattttcgg atctgatcaa    5340
gagacaggat gaggatcgtt tcgcatgatt gaacaagatg gattgcacgc aggttctccg    5400
gccgcttggg tggagaggct attcggctat gactgggcac aacagacaat cggctgctct    5460
gatgccgccg tgttccggct gtcagcgcag gggcgcccgg ttcttttgt caagaccgac    5520
ctgtccggtg ccctgaatga actgcaggac gaggcagcgc ggctatcgtg gctggccacg    5580
acgggcgttc cttgcgcagc tgtgctcgac gttgtcactg aagcgggaag ggactggctg    5640
ctattgggcg aagtgccggg gcaggatctc ctgtcatctc accttgctcc tgccgagaaa    5700
gtatccatca tggctgatgc aatgcggcgg ctgcatacgc ttgatccggc tacctgccca    5760
ttcgaccacc aagcgaaaca tcgcatcgag cgagcacgta ctcggatgga agccggtctt    5820
gtcgatcagg atgatctgga cgaagagcat caggggctcg cgccagccga actgttcgcc    5880
```

```
aggctcaagg cgcgcatgcc cgacggcgag gatctcgtcg tgacccatgg cgatgcctgc    5940
ttgccgaata tcatggtgga aaatggccgc ttttctggat tcatcgactg tggccggctg    6000
ggtgtggcgg accgctatca ggacatagcg ttggctaccc gtgatattgc tgaagagctt    6060
ggcggcgaat gggctgaccg cttcctcgtg ctttacggta tcgccgctcc cgattcgcag    6120
cgcatcgcct tctatcgcct tcttgacgag ttcttctgag cgggactctg gggttcgaaa    6180
tgaccgacca agcgacgccc aacctgccat cacgagattt cgattccacc gccgccttct    6240
atgaaaggtt gggcttcgga atcgttttcc gggacgccgg ctggatgatc ctccagcgcg    6300
gggatctcat gctggagttc ttcgcccacc ccaacttgtt tattgcagct tataatggtt    6360
acaaataaag caatagcatc acaaatttca caaataaagc attttttttca ctgcattcta    6420 gttgtggttt gtccaaactc atcaatgtat cttatcatgt ctgtataccg tcgacctcta    6480
gctagagctt ggcgtaatca tggtcatagc tgtttcctgt gtgaaattgt tatccgctca    6540
caattccaca acatacga gccggaagca taaagtgtaa agcctggggt gcctaatgag     6600
tgagctaact cacattaatt gcgttgcgct cactgcccgc tttccagtcg ggaaacctgt    6660
cgtgccagct gcattaatga atcggccaac gcgcggggag aggcggtttg cgtattgggc    6720
gctcttccgc ttcctcgctc actgactcgc tgcgctcggt cgttcggctg cggcgagcgg    6780
tatcagctca ctcaaaggcg gtaatacggt tatccacaga atcaggggat aacgcaggaa    6840
agaacatgtg agcaaaaggc cagcaaaagg ccaggaaccg taaaaaggcc gcgttgctgg    6900 cgttttttcca taggctccgc ccccctgacg agcatcacaa aaatcgacgc tcaagtcaga    6960
ggtggcgaaa cccgacagga ctataaagat accaggcgtt tccccctgga agctccctcg    7020
tgcgctctcc tgttccgacc ctgccgctta ccggatacct gtccgccttt ctcccttcgg    7080
gaagcgtggc gctttctcat agctcacgct gtaggtatct cagttcggtg taggtcgttc    7140
gctccaagct gggctgtgtg cacgaacccc ccgttcagcc cgaccgctgc gccttatccg    7200
gtaactatcg tcttgagtcc aacccggtaa gacacgactt atcgccactg gcagcagcca    7260
ctggtaacag gattagcaga gcgaggtatg taggcggtgc tacagagttc ttgaagtggt    7320
ggcctaacta cggctacact agaagaacag tatttggtat ctgcgctctg ctgaagccag    7380
ttaccttcgg aaaaagagtt ggtagctctt gatccggcaa acaaaccacc gctggtagcg    7440 gttttttttgt ttgcaagcag cagattacgc gcagaaaaaa aggatctcaa gaagatcctt    7500
tgatcttttc tacggggtct gacgctcagt ggaacgaaaa ctcacgttaa gggattttgg    7560
tcatgagatt atcaaaaagg atcttcacct agatcctttt aaattaaaaa tgaagtttta    7620
aatcaatcta agtatatat gagtaaactt ggtctgacag ttaccaatgc ttaatcagtg    7680
aggcacctat ctcagcgatc tgtctatttc gttcatccat agttgcctga ctccccgtcg    7740
tgtagataac tacgatacgg gagggcttac catctggccc cagtgctgca atgataccgc    7800
gagacccacg ctcaccggct ccagatttat cagcaataaa ccagccagcc ggaagggccg    7860
agcgcagaag tggtcctgca actttatccg cctccatcca gtctattaat tgttgccggg    7920
aagctagagt aagtagttcg ccagttaata gtttgcgcaa cgttgttgcc attgctacag    7980
gcatcgtggt gtcacgctcg tcgtttggta tggcttcatt cagctccggt tcccaacgat    8040
caaggcgagt tacatgatcc cccatgttgt gcaaaaaagc ggttagctcc ttcggtcctc    8100
cgatcgttgt cagaagtaag ttggccgcag tgttatcact catggttatg gcagcactgc    8160
ataattctct tactgtcatg ccatccgtaa gatgcttttc tgtgactggt gagtactcaa    8220
ccaagtcatt ctgagaatag tgtatgcggc gaccgagttg ctcttgcccg gcgtcaatac    8280
```

```
gggataatac cgcgccacat agcagaactt taaaagtgct catcattgga aacgttctt    8340 cggggcgaaa actctcaagg atcttaccgc tgttgagatc cagttcgatg taacccactc   8400
gtgcacccaa ctgatcttca gcatctttta ctttcaccag cgtttctggg tgagcaaaaa   8460
caggaaggca aaatgccgca aaaaagggaa taagggcgac acggaaatgt tgaatactca   8520
tactcttcct ttttcaatat tattgaagca tttatcaggg ttattgtctc atgagcggat   8580
acatatttga atgtatttag aaaaataaac aaatagggg tccgcgcaca tttccccgaa   8640
aagtgccacc tgacgtc                                                  8657
```

<210> SEQ ID NO 4
<211> LENGTH: 8691
<212> TYPE: DNA
<213> ORGANISM: Artificial Sequence
<220> FEATURE:
<223> OTHER INFORMATION: Synthetic construct of x6GC/GEPO vector

<400> SEQUENCE: 4

```
gacggatcgg gagatcccat agtcccgccc ctaactccgc ccatcccgcc cctaactccg     60
cccagttccg cccattctcc gccccatggc tgactaattt ttttatttta tgcagaggcc    120
gaggccgcct ctgcctctga gctattccag aagtagtgag gaggcttttt tggaggccta    180
ggcttttgca aaaagctccc gggatggttc gaccattgaa ctgcatcgtc gccgtgtccc    240
aaaatatggg gattggcaag aacggaaacc taccctggcc tccgctcagg aacgagttca    300
agtacttcca agaatgacc acaacctctt cagtggaagg taaacagaat ctggtgatta    360
tgggtaggaa aacctggttc tccattcctg agaagaatcg accttaaag gacagaatta     420 atatagttct cagtagagaa ctcaaagaac caccacgagg agctcatttt cttgccaaaa    480
gtttggatga tgccttaaga cttattgaac aaccggaatt ggcaagtaaa gtagacatgg    540
tttggatagt cggaggcagt tctgtttacc aggaagccat gaatcaacca ggccacctca    600
gactctttgt gacaaggatc atgcaggaat ttgaaagtga cacgtttttc ccagaaattg    660
atttggggaa atataaactt ctcccagaat acccaggcgt cctctctgag tccaggagg     720 aaaaaggcat caagtataag tttgaagtct acgagaagaa agactaacag gttcgaaatg    780
accgaccaag cgacgcccaa cctgccatca cgagatttcg attccaccgc cgccttctat    840
gaaaggttgg gcttcggaat cgtttttccgg gacgccggct gatgatcct ccagcgcggg   900 gatctcatgc tggagttctt cgcccaccc aacttgttta ttgcagctta taatggttac    960
aaataaagca atagcatcac aaatttcaca ataaagcat ttttttcact gcattctagt   1020
tgtggtttgt ccaaactcat caatgtatct tatcatgtct gggatctccc gatcccctat   1080
ggtgcactct cagtacaatc tgctctgatg ccgcatagtt aagccagtat ctgctccctg   1140
cttgtgtgtt ggaggtcgct gagtagtgcg cgagcaaaat ttaagctaca acaaggcaag   1200
gcttgaccga caattgcatg aagaatctgc ttagggttag gcgttttgcg ctgcttcgcg   1260
atgtacgggc cagatatacg cgttgacatt gattattgac tagttattaa tagtaatcaa   1320
ttacggggtc attagttcat agcccatata tggagttccg cgttacataa cttacggtaa   1380
atggcccgcc tggctgaccg cccaacgacc cccgcccatt gacgtcaata atgacgtatg   1440
ttcccatagt aacgccaata gggactttcc attgacgtca atgggtggag tatttacggt   1500
aaactgccca cttggcagta catcaagtgt atcatatgcc aagtacgccc cctattgacg   1560
tcaatgacgg taaatggccc gcctggcatt atgcccagta catgacctta tgggactttc   1620
```

```
ctacttggca gtacatctac gtattagtca tcgctattac catggtgatg cggttttggc    1680
agtacatcaa tgggcgtgga tagcggtttg actcacgggg atttccaagt ctccacccca    1740
ttgacgtcaa tgggagtttg ttttggcacc aaaatcaacg ggactttcca aaatgtcgta    1800
acaactccgc cccattgacg caaatgggcg gtaggcgtgt acggtgggag gtctatataa    1860
gcagagctct ctggctaact agagaaccca ctgcttactg gcttatcgaa attaatacga    1920
ctcactatag ggagacccaa gctggctagc gtttaaactt aagcttggta ccgagctcgg    1980
atccactagt aacggccgcc agtgtgctgg aattctgcag attcgaggtc gacggtatcg    2040
ataagcttcc aagcgcggag atgggggtgc acggtgagta ctcgcgggct gggcgctccc    2100
gcccgcccgg gtccctgttt gagcgggat ttagcgcccc ggctattggc caggaggtgg    2160
ctgggttcaa ggaccggcga cttgtcaagg accccggaag ggggaggggg gtggggcagc    2220
ctccacgtgc cagcggggac ttgggggagt ccttggggat ggcaaaaacc tgacctgtga    2280
aggggacaca gtttgggggt tgaggggaag aaggtttggg ggttctgctg tgccagtgga    2340
gaggaagctg ataagctgat aacctgggcg ctggagccac cacttatctg ccagagggga    2400
agcctctgtc acaccaggat tgaagtttgg ccggagaagt ggatgctggt agctgggggt    2460
ggggtgtgca cacggcagca ggattgaatg aaggccaggg aggcagcacc tgagtgcttg    2520
catggttggg gacaggaagg acgagctggg gcagagacgt ggggatgaag gaagctgtcc    2580
ttccacagcc acccttctcc ctccccgcct gactctcagc ctggctatct gttctagaat    2640
gtcctgcctg gctgtggctt ctcctgtccc tgctgtcgct ccctctgggc ctcccagtcc    2700
tgggcgcccc accacgcctc atctgtgaca gccgagtcct ggagaggtac ctcttggagg    2760
ccaaggaggc cgagaatatc acggtgagac cccttcccca gcacattcca cagaactcac    2820
gctcagggct tcaggaact cctcccagat ccaggaacct ggcacttggt ttagggtgga    2880
gttgggaagc tagacactgc cccctacat aagaataagt ctggtggccc caaaccatac    2940
ctggaaacta ggcaaggagc aaagccagca gatcctacgg cctgtgggcc agggccagag    3000
ccttcaggga cccttgactc cccgggctgt gtgcatttca gacgggctgt gctgaacact    3060
gcagcttgaa tgagaatatc actgtcccag acaccaaagt taatttctat gcctggaaga    3120
ggatggaggt gagttccttt tttttttttt ttcctttctt ttggagaatc tcatttgcga    3180
gcctgatttt ggatgaaagg gagaatgatc gagggaaagg taaatggag cagcagagat    3240
gaggctgcct gggcgcagag gctcacgtct ataatcccag gctgagatgg ccgagatggg    3300
agaattgctt gagccctgga gtttcagacc aacctaggca gcatagtgag atccccatc    3360
tctacaaaca tttaaaaaaa ttagtcaggt gaagtggtgc atggtggtag tcccagatat    3420
ttggaaggct gaggcgggag gatcgcttga gcccaggaat ttgaggctgc agtgagctgt    3480
gatcacacca ctgcactcca gcctcagtga cagagtgagg ccctgtctca aaaagaaaa    3540
gaaaaaagaa aaataatgag ggctgtatgg aatacattca ttattcattc actcactcac    3600
tcactcattc attcattcat tcattcaaca agtcttattg cataccttct gtttgctcag    3660
cttggtgctt ggggctgctg aggggcagga gggagaggggt gacatgggtc agctgactcc    3720
cagagtccac tccctgtagg tcggcagca ggccgtagaa gtctggcagg gcctggccct    3780
gctgtcggaa gctgtcctgc ggggccaggc cctgttggtc aactcttccc agccgtggga    3840
gcccctgcag ctgcatgtgg ataaagccgt cagtggcctt cgcagcctca ccactctgct    3900
tcgggctctg ggacccagg tgagtaggag cggacacttc tgcttgccct ttctgtaaga    3960
aggggagaag ggtcttgcta aggagtacag gaactgtccg tattccttcc ctttctgtgg    4020
```

```
cactgcagcg acctcctgtt ttctccttgg cagaaggaag ccatctcccc tccagatgcg   4080
gcctcagctg ctccactccg aacaatcact gctgacactt tccgcaaact cttccgagtc   4140
tactccaatt tcctccgggg aaagctgaag ctgtacacag gggaggcctg caggacaggg   4200
gacagatgac cagcttgata tcgaattatc catcacactg gcggccgctc gagtctagag   4260
ggcccgttta aacccgctga tcagcctcga ctgtgccttc tagttgccag ccatctgttg   4320
tttgcccctc cccgtgcct tccttgaccc tggaaggtgc cactcccact gtcctttcct   4380
aataaaatga ggaaattgca tcgcattgtc tgagtaggtg tcattctatt ctggggggtg   4440
gggtggggca ggacagcaag ggggaggatt gggaagacaa tagcaggcat gctgggatg   4500 cggtgggctc tatggcttct gaggcggaaa gaaccagctg gggctctagg gggtatcccc   4560
acgcgccctg tagcggcgca ttaagcgcgg cgggtgtggt ggttacgcgc agcgtgaccg   4620
ctacacttgc cagcgcccta gcgcccgctc ctttcgcttt cttcccttcc tttctcgcca   4680
cgttcgccgg ctttccccgt caagctctaa atcgggggct ccctttaggg ttccgattta   4740
gtgctttacg gcacctcgac cccaaaaaac ttgattaggg tgatggttca cgtagtgggc   4800
catcgccctg atagacggtt tttcgccctt gacgttgga gtccacgttc tttaatagtg   4860
gactcttgtt ccaaactgga acaacactca accctatctc ggtctattct tttgatttat   4920
aagggatttt gccgatttcg gcctattggt taaaaatga gctgatttaa caaaattta   4980 acgcgaatta attctgtgga atgtgtgtca gttagggtgt ggaaagtccc caggctcccc   5040
agcaggcaga agtatgcaaa gcatgcatct caattagtca gcaaccaggt gtggaaagtc   5100
cccaggctcc ccagcaggca gaagtatgca aagcatgcat ctcaattagt cagcaaccat   5160
agtcccgccc ctaactccgc ccatcccgcc cctaactccg cccagttccg cccattctcc   5220
gccccatggc tgactaattt ttttatttta tgcagaggcc gaggccgcct ctgcctctga   5280
gctattccag aagtagtgag gaggcttttt tggaggccta ggcttttgca aaaagctccc   5340
gggagcttgt atatccattt tcggatctga tcaagagaca ggatgaggat cgtttcgcat   5400
gattgaacaa gatggattgc acgcaggttc tccggccgct tgggtggaga ggctattcgg   5460
ctatgactgg gcacaacaga caatcggctg ctctgatgcc gccgtgttcc ggctgtcagc   5520
gcaggggcgc ccggttcttt ttgtcaagac cgacctgtcc ggtgccctga atgaactgca   5580
ggacgaggca gcgcggctat cgtggctggc cacgacgggc gttccttgcg cagctgtgct   5640
cgacgttgtc actgaagcgg gaagggactg gctgctattg ggcgaagtgc cggggcagga   5700
tctcctgtca tctcaccttg ctcctgccga gaaagtatcc atcatggctg atgcaatgcg   5760
gcggctgcat acgcttgatc cggctacctg cccattcgac caccaagcga aacatcgcat   5820
cgagcgagca cgtactcgga tggaagccgg tcttgtcgat caggatgatc tggacgaaga   5880
gcatcagggg ctcgcgccag ccgaactgtt cgccaggctc aaggcgcgca tgcccgacgg   5940
cgaggatctc gtcgtgaccc atggcgatgc ctgcttgccg aatatcatgg tggaaaatgg   6000
ccgcttttct ggattcatcg actgtggccg gctgggtgtg gcggaccgct atcaggacat   6060
agcgttggct acccgtgata ttgctgaaga gcttggcggc gaatgggctg accgcttcct   6120
cgtgctttac ggtatcgccg ctcccgattc gcagcgcatc gccttctatc gccttcttga   6180
cgagttcttc tgagcgggac tctgggttc gaaatgaccg accaagcgac gcccaacctg   6240
ccatcacgag atttcgattc caccgccgcc ttctatgaaa ggttgggctt cggaatcgtt   6300
ttccgggacg ccggctggat gatcctccag cgcggggatc tcatgctgga gttcttcgcc   6360
```

```
cacccccaact tgtttattgc agcttataat ggttacaaat aaagcaatag catcacaaat    6420
ttcacaaata aagcattttt ttcactgcat tctagttgtg gtttgtccaa actcatcaat    6480
gtatcttatc atgtctgtat accgtcgacc tctagctaga gcttggcgta atcatggtca    6540
tagctgtttc ctgtgtgaaa ttgttatccg ctcacaattc cacacaacat acgagccgga    6600
agcataaagt gtaaagcctg gggtgcctaa tgagtgagct aactcacatt aattgcgttg    6660
cgctcactgc ccgctttcca gtcgggaaac ctgtcgtgcc agctgcatta atgaatcggc    6720
caacgcgcgg ggagaggcgg tttgcgtatt gggcgctctt ccgcttcctc gctcactgac    6780
tcgctgcgct cggtcgttcg gctgcggcga gcggtatcag ctcactcaaa ggcggtaata    6840
cggttatcca cagaatcagg ggataacgca ggaaagaaca tgtgagcaaa aggccagcaa    6900
aaggccagga accgtaaaaa ggccgcgttg ctggcgtttt tccataggct ccgcccccct    6960
gacgagcatc acaaaaatcg acgctcaagt cagaggtggc gaaacccgac aggactataa    7020
agataccagg cgtttccccc tggaagctcc ctcgtgcgct ctcctgttcc gaccctgccg    7080
cttaccggat acctgtccgc ctttctccct tcgggaagcg tggcgctttc tcatagctca    7140
cgctgtaggt atctcagttc ggtgtaggtc gttcgctcca agctgggctg tgtgcacgaa    7200
ccccccgttc agcccgaccg ctgcgcctta tccggtaact atcgtcttga gtccaacccg    7260
gtaagacacg acttatcgcc actggcagca gccactggta acaggattag cagagcgagg    7320
tatgtaggcg gtgctacaga gttcttgaag tggtggccta actacggcta cactagaaga    7380
acagtatttg gtatctgcgc tctgctgaag ccagttacct tcggaaaaag agttggtagc    7440
tcttgatccg gcaaacaaac caccgctggt agcggttttt ttgtttgcaa gcagcagatt    7500
acgcgcagaa aaaaggatc tcaagaagat cctttgatct tttctacggg gtctgacgct    7560
cagtggaacg aaaactcacg ttaagggatt ttggtcatga gattatcaaa aaggatcttc    7620
acctagatcc ttttaaatta aaaatgaagt tttaaatcaa tctaaagtat atatgagtaa    7680
acttggtctg acagttacca atgcttaatc agtgaggcac ctatctcagc gatctgtcta    7740
tttcgttcat ccatagttgc ctgactcccc gtcgtgtaga taactacgat acgggagggc    7800
ttaccatctg gccccagtgc tgcaatgata ccgcgagacc cacgctcacc ggctccagat    7860
ttatcagcaa taaaccagcc agccggaagg gccgagcgca gaagtggtcc tgcaacttta    7920
tccgcctcca tccagtctat taattgttgc cgggaagcta gagtaagtag ttcgccagtt    7980
aatagtttgc gcaacgttgt tgccattgct acaggcatcg tggtgtcacg ctcgtcgttt    8040
ggtatggctt cattcagctc cggttcccaa cgatcaaggc gagttacatg atcccccatg    8100
ttgtgcaaaa aagcggttag ctccttcggt cctccgatcg ttgtcagaag taagttggcc    8160
gcagtgttat cactcatggt tatggcagca ctgcataatt ctcttactgt catgccatcc    8220
gtaagatgct tttctgtgac tggtgagtac tcaaccaagt cattctgaga atagtgtatg    8280
cggcgaccga gttgctcttg cccggcgtca atacgggata ataccgcgcc acatagcaga    8340
actttaaaag tgctcatcat tggaaaacgt tcttcgggge gaaaactctc aaggatctta    8400
ccgctgttga gatccagttc gatgtaaccc actcgtgcac ccaactgatc ttcagcatct    8460
tttactttca ccagcgtttc tgggtgagca aaaacaggaa ggcaaaatgc cgcaaaaaag    8520
ggaataaggg cgacacggaa atgttgaata ctcatactct tcctttttca atattattga    8580
agcatttatc agggttattg tctcatgagc ggatacatat ttgaatgtat ttagaaaaat    8640
aaacaaatag gggttccgcg cacatttccc cgaaaagtgc cacctgacgt c              8691
```

<210> SEQ ID NO 5
<211> LENGTH: 7022
<212> TYPE: DNA
<213> ORGANISM: Artificial Sequence
<220> FEATURE:
<223> OTHER INFORMATION: Synthetic construct of X0GC/dhfr vector

<400> SEQUENCE: 5

```
gacggatcgg agatccgac  atgataagat  acattgatga  gtttggacaa  accacaacta     60
gaatgcagtg aaaaaaatgc tttatttgtg aaatttgtga tgctattgct ttatttgtaa    120
ccattataag ctgcaataaa caagttaaca acaacaattg cattcatttt atgtttcagg    180
ttcaggggga ggtgtgggag gttttttaaa gcaagtaaaa cctctacaaa tgtggtatgg    240
ctgattatga tctctagtca aggcactata catcaaatat tccttattaa cccctttaca    300
aattaaaaag ctaaaggtac acaattttg  agcatagtta ttaatagcag acactctatg    360
cctgtgtgga gtaagaaaaa acagtatgtt atgattataa ctgttatgcc tacttataaa    420
ggttacagaa tattttttcca taattttctt gtatagcagt gcagcttttt cctttgtggt    480
gtaaatagca aagcaagcaa gagttctatt actaaacaca gcatgactca aaaaacttag    540
caattctgaa ggaaagtcct tggggtcttc tacctttctc ttcttttttg gaggagtaga    600
atgttgagag tcagcagtag cctcatcatc actagatggc atttcttctg agcaaaacag    660
gttttcctca ttaaaggcat tccaccactg ctcccattca tcagttccat aggttggaat    720
ctaaaataca caaacaatta gaatcagtag tttaacacat tatacactta aaaatttat    780
atttaccta  gagctttaaa tctctgtagg tagtttgtcc aattatgtca caccacagaa    840
gtaaggttcc ttcacaaaga tccaaagcca gcaaagtcc  catggtctta taaaaatgca    900
tagctttagg aggggagcag agaacttgaa agcatcttcc tgttagtctt tcttctcgta    960
gacttcaaac ttatacttga tgccttttttc ctcctggacc tcagagagga cgcctgggta   1020
ttctgggaga agtttatatt tccccaaatc aatttctggg aaaaacgtgt cactttcaaa   1080
ttcctgcatg atccttgtca caaagagtct gaggtggcct ggttgattca tggcttcctg   1140
gtaaacagaa ctgcctccga ctatccaaac catgtctact ttacttgcca attccgttg    1200
ttcaataagt cttaaggcat catccaaact tttggcaaga aaatgagctc ctcgtggtgg   1260
ttctttgagt tctctactga gaactatatt aattctgtcc tttaaggtc  gattcttctc   1320
aggaatggag aaccaggttt tcctacccat aatcaccaga ttctgtttac cttccactga   1380
agaggttgtg gtcattcttt ggaagtactt gaactcgttc ctgagcggag gccagggtag   1440
gtctccgttc ttgccaatcc ccatattttg ggacacggcg acgatgcagt caatggtcg    1500
aaccatgatg gcagcgggga taaaatccta ccagccttca cgctaggatt gccgtcaagt   1560
ttggcgcgaa atcgcagccc tgagctgtgg atctcccgat cccctatggt gcactctcag   1620
tacaatctgc tctgatgccg catagttaag ccagtatctg ctccctgctt gtgtgttgga   1680
ggtcgctgag tagtgcgcga gcaaaattta agctacaaca aggcaaggct tgaccgacaa   1740
ttgcatgaag aatctgctta gggttaggcg ttttgcgctg cttcgcgatg tacgggccag   1800
atatacgcgt tgacattgat tattgactag ttattaatag taatcaatta cggggtcatt   1860
agttcatagc ccatatatgg agttccgcgt tacataactt acggtaaatg gcccgcctgg   1920
ctgaccgccc aacgaccccc gcccattgac gtcaataatg acgtatgttc ccatagtaac   1980
gccaataggg actttccatt gacgtcaatg ggtggagtat ttacggtaaa ctgcccactt   2040
ggcagtacat caagtgtatc atatgccaag tacgccccct attgacgtca atgacggtaa   2100
```

```
atggcccgcc tggcattatg cccagtacat gaccttatgg gactttccta cttggcagta      2160
catctacgta ttagtcatcg ctattaccat ggtgatgcgg ttttggcagt acatcaatgg      2220
gcgtggatag cggtttgact cacggggatt tccaagtctc caccccattg acgtcaatgg      2280
gagtttgttt tggcaccaaa atcaacggga ctttccaaaa tgtcgtaaca actccgcccc      2340
attgacgcaa atgggcggta ggcgtgtacg gtgggaggtc tatataagca gagctctctg      2400
gctaactaga acccactg cttactggct tatcgaaatt aatacgactc actataggga      2460
gacccaagct tggtaccgag ctcggatcca ctagtaacgg ccgccagtgt gctggaattc      2520
tgcagatatc catcacactg gcggccgctc gagcatgcat ctagagggcc ctattctata      2580
gtgtcaccta aatgctagag ctcgctgatc agcctcgact gtgccttcta gttgccagcc      2640
atctgttgtt tgcccctccc ccgtgccttc cttgaccctg gaaggtgcca ctcccactgt      2700
cctttcctaa taaaatgagg aaattgcatc gcattgtctg agtaggtgtc attctattct      2760
ggggggtggg gtggggcagg acagcaaggg ggaggattgg gaagacaata gcaggcatgc      2820
tggggatgcg gtgggctcta tggcttctga ggcggaaaga accagctggg gctctagggg      2880
gtatccccac gcgccctgta gcggcgcatt aagcgcggcg ggtgtggtgg ttacgcgcag      2940
cgtgaccgct acacttgcca gcgccctagc gcccgctcct ttcgctttct tcccttcctt      3000
tctcgccacg ttcgccggct ttccccgtca agctctaaat cggggggctcc ctttagggtt      3060
ccgatttagt gctttacggc acctcgaccc caaaaaactt gattagggtg atggttcacg      3120
tagtgggcca tcgccctgat agacggtttt tcgcccttg acgttggagt ccacgttctt      3180
taatagtgga ctcttgttcc aaactggaac aacactcaac cctatctcgg tctattcttt      3240
tgatttataa gggattttgc cgatttcggc ctattggtta aaaaatgagc tgatttaaca      3300
aaaatttaac gcgaattaat tctgtggaat gtgtgtcagt tagggtgtgg aaagtcccca      3360
ggctccccag caggcagaag tatgcaaagc atgcatctca attagtcagc aaccaggtgt      3420
ggaaagtccc caggctcccc agcaggcaga agtatgcaaa gcatgcatct caattagtca      3480
gcaaccatag tcccgcccct aactccgccc atcccgcccc taactccgcc cagttccgcc      3540
cattctccgc cccatggctg actaattttt tttatttatg cagaggccga ggccgcctct      3600
gcctctgagc tattccagaa gtagtgagga ggcttttttg gaggcctagg cttttgcaaa      3660
aagctcccgg gagcttgtat atccattttc ggatctgatc aagagacagg atgaggatcg      3720
tttcgcatga ttgaacaaga tggattgcac gcaggttctc cggccgcttg ggtggagagg      3780
ctattcggct atgactgggc acaacagaca atcggctgct ctgatgccgc cgtgttccgg      3840
ctgtcagcgc aggggcgccc ggttcttttt gtcaagaccg acctgtccgg tgccctgaat      3900
gaactgcagg acgaggcagc gcggctatcg tggctggcca cgacgggcgt tccttgcgca      3960
gctgtgctcg acgttgtcac tgaagcggga agggactggc tgctattggg cgaagtgccg      4020
gggcaggatc tcctgtcatc tcaccttgct cctgccgaga aagtatccat catggctgat      4080
gcaatgcggc ggctgcatac gcttgatccg gctacctgcc cattcgacca ccaagcgaaa      4140
catcgcatcg agcgagcacg tactcggatg gaagccggtc ttgtcgatca ggatgatctg      4200
gacgaagagc atcaggggct cgcgccagcc gaactgttcg ccaggctcaa ggcgcgcatg      4260
cccgacggcg aggatctcgt cgtgacccat ggcgatgcct gcttgccgaa tatcatggtg      4320
gaaaatggcc gcttttctgg attcatcgac tgtggccggc tgggtgtggc ggaccgctat      4380
caggacatag cgttggctac ccgtgatatt gctgaagagc ttggcggcga atgggctgac      4440
cgcttcctcg tgctttacgg tatcgccgct cccgattcgc agcgcatcgc cttctatcgc      4500
```

```
cttcttgacg agttcttctg agcgggactc tggggttcga aatgaccgac caagcgacgc    4560
ccaacctgcc atcacgagat ttcgattcca ccgccgcctt ctatgaaagg ttgggcttcg    4620
gaatcgtttt ccgggacgcc ggctggatga tcctccagcg cggggatctc atgctggagt    4680
tcttcgccca ccccaacttg tttattgcag cttataatgg ttacaaataa agcaatagca    4740
tcacaaattt cacaaataaa gcattttttt cactgcattc tagttgtggt ttgtccaaac    4800
tcatcaatgt atcttatcat gtctgtatac cgtcgacctc tagctagagc ttggcgtaat    4860
catggtcata gctgtttcct gtgtgaaatt gttatccgct cacaattcca cacaacatac    4920
gagccggaag cataaagtgt aaagcctggg gtgcctaatg agtgagctaa ctcacattaa    4980
ttgcgttgcg ctcactgccc gctttccagt cgggaaacct gtcgtgccag ctgcattaat    5040
gaatcggcca acgcgcgggg agaggcggtt tgcgtattgg gcgctcttcc gcttcctcgc    5100
tcactgactc gctgcgctcg gtcgttcggc tgcggcgagc ggtatcagct cactcaaagg    5160
cggtaatacg gttatccaca gaatcagggg ataacgcagg aaagaacatg tgagcaaaag    5220
gccagcaaaa ggccaggaac cgtaaaaagg ccgcgttgct ggcgtttttc cataggctcc    5280
gcccccctga cgagcatcac aaaaatcgac gctcaagtca gaggtggcga aacccgacag    5340
gactataaag ataccaggcg tttccccctg gaagctccct cgtgcgctct cctgttccga    5400
ccctgccgct taccggatac ctgtccgcct ttctcccttc gggaagcgtg gcgctttctc    5460
atagctcacg ctgtaggtat ctcagttcgg tgtaggtcgt tcgctccaag ctgggctgtg    5520
tgcacgaacc ccccgttcag cccgaccgct gcgccttatc cggtaactat cgtcttgagt    5580
ccaacccggt aagacacgac ttatcgccac tggcagcagc cactggtaac aggattagca    5640
gagcgaggta tgtaggcggt gctacagagt tcttgaagtg gtggcctaac tacggctaca    5700
ctagaagaac agtatttggt atctgcgctc tgctgaagcc agttaccttc ggaaaaagag    5760
ttggtagctc ttgatccggc aaacaaacca ccgctggtag cggtggtttt tttgtttgca    5820
agcagcagat tacgcgcaga aaaaaaggat ctcaagaaga tcctttgatc ttttctacgg    5880
ggtctgacgc tcagtggaac gaaaactcac gttaagggat tttggtcatg agattatcaa    5940
aaaggatctt cacctagatc cttttaaatt aaaaatgaag ttttaaatca atctaaagta    6000
tatatgagta aacttggtct gacagttacc aatgcttaat cagtgaggca cctatctcag    6060
cgatctgtct atttcgttca tccatagttg cctgactccc cgtcgtgtag ataactacga    6120
tacgggaggg cttaccatct ggccccagtg ctgcaatgat accgcgagac ccacgctcac    6180
cggctccaga tttatcagca ataaaccagc cagccggaag ggccgagcgc agaagtggtc    6240
ctgcaacttt atccgcctcc atccagtcta ttaattgttg ccgggaagct agagtaagta    6300
gttcgccagt taatagtttg cgcaacgttg ttgccattgc tacaggcatc gtggtgtcac    6360
gctcgtcgtt tggtatggct tcattcagct ccggttccca acgatcaagg cgagttacat    6420
gatcccccat gttgtgcaaa aaagcggtta gctccttcgg tcctccgatc gttgtcagaa    6480
gtaagttggc cgcagtgtta tcactcatgg ttatggcagc actgcataat tctcttactg    6540
tcatgccatc cgtaagatgc ttttctgtga ctggtgagta ctcaaccaag tcattctgag    6600
aatagtgtat gcggcgaccg agttgctctt gcccggcgtc aatacgggat aataccgcgc    6660
cacatagcag aactttaaaa gtgctcatca ttggaaaacg ttcttcgggg cgaaaactct    6720
caaggatctt accgctgttg agatccagtt cgatgtaacc cactcgtgca cccaactgat    6780
cttcagcatc ttttactttc accagcgttt ctgggtgagc aaaaacagga aggcaaaatg    6840
```

-continued

| | |
|---|---|
| ccgcaaaaaa gggaataagg gcgacacgga aatgttgaat actcatactc ttcctttttc | 6900 |
| aatattattg aagcatttat cagggttatt gtctcatgag cggatacata tttgaatgta | 6960 |
| tttagaaaaa taaacaaata ggggttccgc gcacatttcc ccgaaaagtg ccacctgacg | 7020 |
| tc | 7022 |

<210> SEQ ID NO 6
<211> LENGTH: 6422
<212> TYPE: DNA
<213> ORGANISM: Artificial Sequence
<220> FEATURE:
<223> OTHER INFORMATION: Synthetic construct of X1GC/dhfr vector

<400> SEQUENCE: 6

| | |
|---|---|
| gacggatcgg gagatccatt ctccgcccca tggctgacta atttttttta tttatgcaga | 60 |
| ggccgaggcc gcctctgcct ctgagctatt ccagaagtag tgaggaggct ttttggagg | 120 |
| cctaggcttt tgcaaaaagc tcccgggatg gttcgaccat tgaactgcat cgtcgccgtg | 180 |
| tcccaaaata tggggattgg caagaacgga aacctaccct ggcctccgct caggaacgag | 240 |
| ttcaagtact ccaaagaat gaccacaacc tcttcagtgg aaggtaaaca gaatctggtg | 300 |
| attatgggta ggaaaacctg gttctccatt cctgagaaga atcgacctt aaaggacaga | 360 |
| attaatatag ttctcagtag agaactcaaa gaaccaccac gaggagctca ttttcttgcc | 420 |
| aaaagtttgg atgatgcctt aagacttatt gaacaaccgg aattggcaag taaagtagac | 480 |
| atggtttgga tagtcggagg cagttctgtt taccaggaag ccatgaatca accaggccac | 540 |
| ctcagactct ttgtgacaag gatcatgcag gaatttgaaa gtgacacgtt tttcccagaa | 600 |
| attgatttgg ggaaatataa acttctccca gaatacccag gcgtcctctc tgaggtccag | 660 |
| gaggaaaaag gcatcaagta taagtttgaa gtctacgaga gaaagacta caggttcga | 720 |
| aatgaccgac caagcgacgc ccaacctgcc atcacgagat ttcgattcca ccgccgcctt | 780 |
| ctatgaaagg ttgggcttcg gaatcgtttt ccgggacgcc ggctggatga tcctccagcg | 840 |
| cggggatctc atgctggagt tcttcgccca ccccaacttg tttattgcag cttataatgg | 900 |
| ttacaaataa agcaatagca tcacaaattt cacaaataaa gcatttttt cactgcattc | 960 |
| tagttgtggt ttgtccaaac tcatcaatgt atcttatcat gtctgggatc tcccgatccc | 1020 |
| ctatggtgca ctctcagtac aatctgctct gatgccgcat agttaagcca gtatctgctc | 1080 |
| cctgcttgtg tgttggaggt cgctgagtag tgcgcgagca aaatttaagc tacaacaagg | 1140 |
| caaggcttga ccgacaattg catgaagaat ctgcttaggg ttaggcgttt tgcgctgctt | 1200 |
| cgcgatgtac gggccagata tacgcgttga cattgattat tgactagtta ttaatagtaa | 1260 |
| tcaattacgg ggtcattagt tcatagccca tatatggagt tccgcgttac ataacttacg | 1320 |
| gtaaatggcc cgcctggctg accgcccaac gacccccgcc cattgacgtc aataatgacg | 1380 |
| tatgttccca tagtaacgcc aatagggact ttccattgac gtcaatgggt ggagtattta | 1440 |
| cggtaaactg cccacttggc agtacatcaa gtgtatcata tgccaagtac gccccctatt | 1500 |
| gacgtcaatg acggtaaatg gcccgcctgg cattatgccc agtacatgac cttatgggac | 1560 |
| tttcctactt ggcagtacat ctacgtatta gtcatcgcta ttaccatggt gatgcggttt | 1620 |
| tggcagtaca tcaatgggcg tggatagcgg tttgactcac ggggatttcc aagtctccac | 1680 |
| cccattgacg tcaatgggag tttgttttgg caccaaaatc aacgggactt tccaaaatgt | 1740 |
| cgtaacaact ccgccccatt gacgcaaatg ggcggtaggc gtgtacgtg ggaggtctat | 1800 |
| ataagcagag ctctctggct aactagagaa cccactgctt actggcttat cgaaattaat | 1860 |

```
acgactcact ataqggagac ccaagctggc tagcgtttaa acttaagctt ggtaccgagc    1920
tcggatccac tagtccagtg tggtggaatt ctgcagatat ccagcacagt ggcggccgct    1980
cgagtctaga gggcccgttt aaacccgctg atcagcctcg actgtgcctt ctagttgcca    2040
gccatctgtt gtttgcccct cccccgtgcc ttccttgacc ctggaaggtg ccactcccac    2100
tgtcctttcc taataaaatg aggaaattgc atcgcattgt ctgagtaggt gtcattctat    2160
tctggggggt ggggtggggc aggacagcaa gggggaggat tgggaagaca atagcaggca    2220
tgctggggat gcggtgggct ctatggcttc tgaggcggaa agaaccagct ggggctctag    2280
ggggtatccc cacgcgccct gtagcggcgc attaagcgcg gcgggtgtgg tggttacgcg    2340
cagcgtgacc gctacacttg ccagcgccct agcgcccgct cctttcgctt tcttcccttc    2400
ctttctcgcc acgttcgccg gctttccccg tcaagctcta aatcgggggc tccctttagg    2460
gttccgattt agtgctttac ggcacctcga ccccaaaaaa cttgattagg gtgatggttc    2520
acgtagtggg ccatcgccct gatagacggt ttttcgccct ttgacgttgg agtccacgtt    2580
ctttaatagt ggactcttgt tccaaactgg aacaacactc aaccctatct cggtctattc    2640
ttttgattta agggatttt tgccgatttc ggcctattgg ttaaaaaatg agctgattta    2700
acaaaaattt aacgcgaatt aattctgtgg aatgtgtgtc agttagggtg tggaaagtcc    2760
ccaggctccc cagcaggcag aagtatgcaa agcatgcatc tcaattagtc agcaaccagg    2820
tgtggaaagt ccccaggctc cccagcaggc agaagtatgc aaagcatgca tctcaattag    2880
tcagcaacca tagtcccgcc cctaactccg cccatcccgc cctaactccg cccagttcc    2940 gcccattctc cgccccatgg ctgactaatt tttttattt atgcagaggc cgaggccgcc    3000
tctgcctctg agctattcca gaagtagtga ggaggctttt ttggaggcct aggcttttgc    3060
aaaaagctcc cgggagcttg tatatccatt ttcggatctg atcaagagac aggatgagga    3120
tcgtttcgca tgattgaaca agatggattg cacgcaggtt ctccggccgc ttgggtggag    3180
aggctattcg gctatgactg ggcacaacag acaatcggct gctctgatgc cgccgtgttc    3240
cggctgtcag cgcaggggcg cccggttctt tttgtcaaga ccgacctgtc cggtgccctg    3300
aatgaactgc aggacgaggc agcgcggcta tcgtggctgg ccacgacggg cgttccttgc    3360
gcagctgtgc tcgacgttgt cactgaagcg ggaagggact ggctgctatt gggcgaagtg    3420
ccggggcagg atctcctgtc atctcacctt gctcctgccg agaaagtatc catcatggct    3480
gatgcaatgc ggcggctgca tacgcttgat ccggctacct gcccattcga ccaccaagcg    3540
aaacatcgca tcgagcgagc acgtactcgg atggaagccg gtcttgtcga tcaggatgat    3600
ctggacgaag agcatcaggg gctcgcgcca gccgaactgt tcgccaggct caaggcgcgc    3660
atgcccgacg gcgaggatct cgtcgtgacc catggcgatg cctgcttgcc gaatatcatg    3720
gtggaaaatg gccgcttttc tggattcatc gactgtggcc ggctgggtgt ggcggaccgc    3780
tatcaggaca tagcgttggc tacccgtgat attgctgaag agcttggcgg cgaatgggct    3840
gaccgcttcc tcgtgcttta cggtatcgcc gctcccgatt cgcagcgcat cgccttctat    3900
cgccttcttg acgagttctt ctgagcggga ctctggggtt cgaaatgacc gaccaagcga    3960
cgcccaacct gccatcacga gatttcgatt ccaccgccgc cttctatgaa aggttgggct    4020
tcggaatcgt tttccgggac gccggctgga tgatcctcca gcgcgggat ctcatgctgg    4080 agttcttcgc ccaccccaac ttgtttattg cagcttataa tggttacaaa taaagcaata    4140
gcatcacaaa tttcacaaat aaagcatttt tttcactgca ttctagttgt ggtttgtcca    4200
```

```
aactcatcaa tgtatcttat catgtctgta taccgtcgac ctctagctag agcttggcgt   4260
aatcatggtc atagctgttt cctgtgtgaa attgttatcc gctcacaatt ccacacaaca   4320
tacgagccgg aagcataaag tgtaaagcct ggggtgccta atgagtgagc taactcacat   4380
taattgcgtt gcgctcactg cccgctttcc agtcgggaaa cctgtcgtgc cagctgcatt   4440
aatgaatcgg ccaacgcgcg gggagaggcg gtttgcgtat gggcgctctt ccgcttcct   4500
cgctcactga ctcgctgcgc tcggtcgttc ggctgcggcg agcggtatca gctcactcaa   4560
aggcggtaat acggttatcc acagaatcag gggataacgc aggaaagaac atgtgagcaa   4620
aaggccagca aaaggccagg aaccgtaaaa aggccgcgtt gctggcgttt ttccataggc   4680
tccgcccccc tgacgagcat cacaaaaatc gacgctcaag tcagaggtgg cgaaacccga   4740
caggactata aagataccag gcgtttcccc ctggaagctc cctcgtgcgc tctcctgttc   4800
cgaccctgcc gcttaccgga tacctgtccg cctttctccc ttcgggaagc gtggcgcttt   4860
ctcatagctc acgctgtagg tatctcagtt cggtgtaggt cgttcgctcc aagctgggct   4920
gtgtgcacga accccccgtt cagcccgacc gctgcgcctt atccggtaac tatcgtcttg   4980
agtccaaccc ggtaagacac gacttatcgc cactggcagc agccactggt aacaggatta   5040
gcagagcgag gtatgtaggc ggtgctacag agttcttgaa gtggtggcct aactacggct   5100
acactagaag aacagtattt ggtatctgcg ctctgctgaa gccagttacc ttcggaaaaa   5160
gagttggtag ctcttgatcc ggcaaacaaa ccaccgctgg tagcggtttt tttgtttgca   5220
agcagcagat tacgcgcaga aaaaaggat ctcaagaaga tcctttgatc ttttctacgg   5280
ggtctgacgc tcagtggaac gaaaactcac gttaagggat tttggtcatg agattatcaa   5340
aaaggatctt cacctagatc cttttaaatt aaaaatgaag ttttaaatca atctaaagta   5400
tatatgagta aacttggtct gacagttacc aatgcttaat cagtgaggca cctatctcag   5460
cgatctgtct atttcgttca tccatagttg cctgactccc cgtcgtgtag ataactacga   5520
tacgggaggg cttaccatct ggccccagtg ctgcaatgat accgcgagac ccacgctcac   5580
cggctccaga tttatcagca ataaaccagc cagccggaag ggccgagcgc agaagtggtc   5640
ctgcaacttt atccgcctcc atccagtcta ttaattgttg ccgggaagct agagtaagta   5700
gttcgccagt taatagtttg cgcaacgttg ttgccattgc tacaggcatc gtggtgtcac   5760
gctcgtcgtt tggtatggct tcattcagct ccggttccca acgatcaagg cgagttacat   5820
gatcccccat gttgtgcaaa aaagcggtta gctccttcgg tcctccgatc gttgtcagaa   5880
gtaagttggc cgcagtgtta tcactcatgg ttatggcagc actgcataat tctcttactg   5940
tcatgccatc cgtaagatgc ttttctgtga ctggtgagta ctcaaccaag tcattctgag   6000
aatagtgtat gcggcgaccg agttgctctt gcccggcgtc aatacgggat aataccgcgc   6060
cacatagcag aactttaaaa gtgctcatca ttggaaaacg ttcttcgggg cgaaaactct   6120
caaggatctt accgctgttg agatccagtt cgatgtaacc cactcgtgca cccaactgat   6180
cttcagcatc ttttactttc accagcgttt ctgggtgagc aaaaacagga aggcaaaatg   6240
ccgcaaaaaa gggaataagg gcgacacgga aatgttgaat actcatactc ttcctttttc   6300
aatattattg aagcatttat cagggttatt gtctcatgag cggatacata tttgaatgta   6360
tttagaaaaa taaacaaata ggggttccgc gcacatttcc ccgaaaagtg ccacctgacg   6420
tc                                                                   6422
```

<210> SEQ ID NO 7
<211> LENGTH: 1572

```
<212> TYPE: DNA
<213> ORGANISM: Artificial Sequence
<220> FEATURE:
<223> OTHER INFORMATION: Synthetic construct of x0GC/dhfr cassette

<400> SEQUENCE: 7
gacatgataa gatacattga tgagtttgga caaaccacaa ctagaatgca gtgaaaaaaa      60
tgctttattt gtgaaatttg tgatgctatt gctttatttg taaccattat aagctgcaat     120
aaacaagtta acaacaacaa ttgcattcat tttatgtttc aggttcaggg ggaggtgtgg     180
gaggtttttt aaagcaagta aaacctctac aaatgtggta tggctgatta tgatctctag     240
tcaaggcact atacatcaaa tattccttat taacccottt acaaattaaa aagctaaagg     300
tacacaattt ttgagcatag ttattaatag cagacactct atgcctgtgt ggagtaagaa     360
aaaacagtat gttatgatta taactgttat gcctacttat aaaggttaca gaatattttt     420
ccataatttt cttgtatagc agtgcagctt tttcctttgt ggtgtaaata gcaaagcaag     480
caagagttct attactaaac acagcatgac tcaaaaaact tagcaattct gaaggaaagt     540
ccttggggtc ttctaccttt ctcttctttt ttggaggagt agaatgttga gagtcagcag     600
tagcctcatc atcactagat ggcatttctt ctgagcaaaa caggttttcc tcattaaagg     660
cattccacca ctgctcccat tcatcagttc cataggttgg aatctaaaat acacaaacaa     720
ttagaatcag tagtttaaca cattatacac ttaaaaattt tatatttacc ttagagcttt     780
aaatctctgt aggtagtttg tccaattatg tcacaccaca gaagtaaggt tccttcacaa     840
agatccaaag ccagcaaaag tcccatggtc ttataaaaat gcatagcttt aggagggggag     900 cagagaactt gaaagcatct tcctgttagt ctttcttctc gtagacttca aacttatact     960
tgatgccttt ttcctcctgg acctcagaga ggacgcctgg gtattctggg agaagtttat    1020
atttccccaa atcaatttct gggaaaaacg tgtcactttc aaattcctgc atgatccttg    1080
tcacaaagag tctgaggtgg cctggttgat tcatggcttc ctggtaaaca gaactgcctc    1140
cgactatcca aaccatgtct actttacttg ccaattccgg ttgttcaata agtcttaagg    1200
catcatccaa acttttggca agaaaatgag ctcctcgtgg tggttctttg agttctctac    1260
tgagaactat attaattctg tccttttaaag gtcgattctt ctcaggaatg gagaaccagg    1320
ttttcctacc cataatcacc agattctgtt taccttccac tgaagaggtt gtggtcattc    1380
tttggaagta cttgaactcg ttcctgagcg gaggccaggg taggtctccg ttcttgccaa    1440
tccccatatt ttgggacacg gcgacgatgc agttcaatgg tcgaaccatg atggcagcgg    1500
ggataaaatc ctaccagcct tcacgctagg attgccgtca gtttggcgc gaaatcgcag     1560 ccctgagctg tg                                                       1572

<210> SEQ ID NO 8
<211> LENGTH: 988
<212> TYPE: DNA
<213> ORGANISM: Artificial Sequence
<220> FEATURE:
<223> OTHER INFORMATION: Synthetic construct of x1GC dhfr cassette

<400> SEQUENCE: 8
attctccgcc ccatggctga ctaatttttt ttatttatgc agaggccgag gccgcctctg      60
cctctgagct attccagaag tagtgaggag gcttttttgg aggcctaggc ttttgcaaaa     120
agctcccggg atggtcgac cattgaactg catcgtcgcc gtgtcccaaa atatggggat      180
tggcaagaac ggaaacctac cctggcctcc gctcaggaac gagttcaagt acttccaaag     240
```

| aatgaccaca acctcttcag tggaaggtaa acagaatctg gtgattatgg gtaggaaaac | 300 |
| ctggttctcc attcctgaga agaatcgacc tttaaaggac agaattaata tagttctcag | 360 |
| tagagaactc aaagaaccac cacgaggagc tcattttctt gccaaaagtt tggatgatgc | 420 |
| cttaagactt attgaacaac cggaattggc aagtaaagta gacatggttt ggatagtcgg | 480 |
| aggcagttct gtttaccagg aagccatgaa tcaaccaggc cacctcagac tctttgtgac | 540 |
| aaggatcatg caggaatttg aaagtgacac gttttttccca gaaattgatt tggggaaata | 600 |
| taaacttctc ccagaatacc caggcgtcct ctctgaggtc caggaggaaa aaggcatcaa | 660 |
| gtataagttt gaagtctacg agaagaaaga ctaacaggtt cgaaatgacc gaccaagcga | 720 |
| cgcccaacct gccatcacga gatttcgatt ccaccgccgc cttctatgaa aggttgggct | 780 |
| tcggaatcgt tttccgggac gccggctgga tgatcctcca gcgcgggat ctcatgctgg | 840 |
| agttcttcgc ccacccccaac ttgttattg cagcttataa tggttacaaa taaagcaata | 900 |
| gcatcacaaa tttcacaaat aaagcatttt tttcactgca ttctagttgt ggtttgtcca | 960 |
| aactcatcaa tgtatcttat catgtctg | 988 |

<210> SEQ ID NO 9
<211> LENGTH: 1010
<212> TYPE: DNA
<213> ORGANISM: Artificial Sequence
<220> FEATURE:
<223> OTHER INFORMATION: Synthetic construct of x3GC dhfr cassette

<400> SEQUENCE: 9

| ctaactccgc ccagttccgc ccattctccg ccccatggct gactaatttt ttttatttat | 60 |
| gcagaggccg aggccgcctc tgcctctgag ctattccaga agtagtgagg aggcttttt | 120 |
| ggaggcctag gcttttgcaa aaagctcccg ggatggttcg accattgaac tgcatcgtcg | 180 |
| ccgtgtccca aaatatgggg attggcaaga acggaaacct accctggcct ccgctcagga | 240 |
| acgagttcaa gtacttccaa agaatgacca caacctcttc agtggaaggt aaacagaatc | 300 |
| tggtgattat gggtaggaaa acctggttct ccattcctga agaatcga cctttaaagg | 360 |
| acagaattaa tagttctc agtagagaac tcaaagaacc accacgagga gctcattttc | 420 |
| ttgccaaaag tttggatgat gccttaagac ttattgaaca accggaattg gcaagtaaag | 480 |
| tagacatggt ttggatagtc ggaggcagtt ctgtttacca ggaagccatg aatcaaccag | 540 |
| gccacctcag actctttgtg acaaggatca tgcaggaatt tgaaagtgac acgttttcc | 600 |
| cagaaattga tttggggaaa tataaacttc tcccagaata cccaggcgtc ctctctgagg | 660 |
| tccaggagga aaaaggcatc aagtataagt ttgaagtcta cgagaagaaa gactaacagg | 720 |
| ttcgaaatga ccgaccaagc gacgcccaac ctgccatcac gagatttcga ttccaccgcc | 780 |
| gccttctatg aaaggttggg cttcggaatc gttttccggg acgccggctg gatgatcctc | 840 |
| cagcgcgggg atctcatgct ggagttcttc gcccacccca acttgtttat tgcagcttat | 900 |
| aatggttaca aataaagcaa tagcatcaca aatttcacaa ataaagcatt tttttcactg | 960 |
| cattctagtt gtggttttgtc caaactcatc aatgtatctt atcatgtctg | 1010 |

<210> SEQ ID NO 10
<211> LENGTH: 1044
<212> TYPE: DNA
<213> ORGANISM: Artificial Sequence
<220> FEATURE:
<223> OTHER INFORMATION: Synthetic construct of x6GC dhfr cassette

<400> SEQUENCE: 10

-continued

```
catagtcccg cccctaactc cgcccatccc gccccctaact ccgcccagtt ccgcccattc    60
tccgccccat ggctgactaa ttttttttat ttatgcagag gccgaggccg cctctgcctc   120
tgagctattc cagaagtagt gaggaggctt ttttggaggc ctaggctttt gcaaaaagct   180
cccgggatgg ttcgaccatt gaactgcatc gtcgccgtgt cccaaaatat ggggattggc   240
aagaacggaa acctaccctg gcctccgctc aggaacgagt tcaagtactt ccaaagaatg   300
accacaacct cttcagtgga aggtaaacag aatctggtga ttatgggtag gaaaacctgg   360
ttctccattc ctgagaagaa tcgaccttta aggacagaa ttaatatagt tctcagtaga   420
gaactcaaag aaccaccacg aggagctcat tttcttgcca aaagtttgga tgatgcctta   480
agacttattg aacaaccgga attggcaagt aaagtagaca tggtttggat agtcggaggc   540
agttctgttt accaggaagc catgaatcaa ccaggccacc tcagactctt tgtgacaagg   600
atcatgcagg aatttgaaag tgacacgttt ttcccagaaa ttgatttggg gaaatataaa   660
cttctcccag aatacccagg cgtcctctct gaggtccagg aggaaaaagg catcaagtat   720
aagtttgaag tctacgagaa gaaagactaa caggttcgaa atgaccgacc aagcgacgcc   780
caacctgcca tcacgagatt tcgattccac cgccgccttc tatgaaaggt tgggcttcgg   840
aatcgttttc cgggacgccg gctggatgat cctccagcgc ggggatctca tgctggagtt   900
cttcgcccac cccaacttgt ttattgcagc ttataatggt tacaaataaa gcaatagcat   960 cacaaattc acaaataaag cattttttc actgcattct agttgtggtt tgtccaaact  1020
catcaatgta tcttatcatg tctg                                        1044
```

```
<210> SEQ ID NO 11
<211> LENGTH: 30
<212> TYPE: DNA
<213> ORGANISM: Artificial Sequence
<220> FEATURE:
<223> OTHER INFORMATION: dhfr 01 primer

<400> SEQUENCE: 11
gcgcccggga tggttcgacc attgaactgc                                    30

<210> SEQ ID NO 12
<211> LENGTH: 34
<212> TYPE: DNA
<213> ORGANISM: Artificial Sequence
<220> FEATURE:
<223> OTHER INFORMATION: dhfr-02 primer

<400> SEQUENCE: 12
cacttagaac ctgttagtct tcttctcgt agac                                34

<210> SEQ ID NO 13
<211> LENGTH: 33
<212> TYPE: DNA
<213> ORGANISM: Artificial Sequence
<220> FEATURE:
<223> OTHER INFORMATION: x 1GC primer

<400> SEQUENCE: 13
tcaggatcca ttctccgccc catggctgac taa                                33

<210> SEQ ID NO 14
<211> LENGTH: 35
<212> TYPE: DNA
<213> ORGANISM: Artificial Sequence
<220> FEATURE:
```

```
<223> OTHER INFORMATION: x 3GC primer

<400> SEQUENCE: 14
catggatcct aactccgccc agttccgccc attct                         35

<210> SEQ ID NO 15
<211> LENGTH: 34
<212> TYPE: DNA
<213> ORGANISM: Artificial Sequence
<220> FEATURE:
<223> OTHER INFORMATION: x6GC primer

<400> SEQUENCE: 15
catggatccc atagtcccgc ccctaactcc gccc                          34

<210> SEQ ID NO 16
<211> LENGTH: 31
<212> TYPE: DNA
<213> ORGANISM: Artificial Sequence
<220> FEATURE:
<223> OTHER INFORMATION: X0GC primer

<400> SEQUENCE: 16
cgatggatcc gacatgataa gatacattga t                             31

<210> SEQ ID NO 17
<211> LENGTH: 31
<212> TYPE: DNA
<213> ORGANISM: Artificial Sequence
<220> FEATURE:
<223> OTHER INFORMATION: X0GCRR primer

<400> SEQUENCE: 17
cgttggatcc acagctcagg gctgcgattt c                             31

<210> SEQ ID NO 18
<211> LENGTH: 33
<212> TYPE: DNA
<213> ORGANISM: Artificial Sequence
<220> FEATURE:
<223> OTHER INFORMATION: BISVpAR primer

<400> SEQUENCE: 18
tcaggatccc agacatgata agatacattg atg                           33
```